(12) United States Patent  
Seppi

(10) Patent No.: US 7,737,972 B2
(45) Date of Patent: Jun. 15, 2010

(54) SYSTEMS AND METHODS FOR DIGITAL VOLUMETRIC LAMINAR TOMOGRAPHY

(75) Inventor: Edward J. Seppi, Portola Valley, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 603 days.

(21) Appl. No.: 11/403,377

(22) Filed: Apr. 13, 2006

(65) Prior Publication Data

US 2007/0253529 A1    Nov. 1, 2007

(51) Int. Cl.
*G06T 17/00*    (2006.01)
(52) U.S. Cl. .................. 345/424; 345/419; 345/420; 345/427
(58) Field of Classification Search .............. 345/418, 345/419, 420, 421, 422, 423, 424; 378/4, 378/5, 7, 8, 9, 19, 146, 147, 165, 168
See application file for complete search history.

(56) References Cited

U.S. PATENT DOCUMENTS

| | | | | |
|---|---|---|---|---|
| 5,117,445 A | * | 5/1992 | Seppi et al. .............. 378/65 |
| 5,414,623 A | * | 5/1995 | Lu et al. ................. 382/131 |
| 5,552,605 A | * | 9/1996 | Arata .................. 250/363.04 |
| 6,173,032 B1 | * | 1/2001 | Besson .................... 378/19 |
| 6,175,761 B1 | | 1/2001 | Frandsen et al. |
| 6,318,892 B1 | * | 11/2001 | Suzuki et al. ............. 378/197 |
| 6,325,758 B1 | * | 12/2001 | Carol et al. ............. 600/439 |
| 6,345,114 B1 | * | 2/2002 | Mackie et al. ............ 382/132 |
| 6,490,476 B1 | * | 12/2002 | Townsend et al. ......... 600/427 |
| 6,539,074 B1 | * | 3/2003 | Yavuz et al. ............... 378/4 |
| 6,807,247 B2 | * | 10/2004 | Krishnan et al. ............ 378/4 |
| 6,879,656 B2 | * | 4/2005 | Cesmeli et al. ............. 378/4 |
| 6,885,886 B2 | * | 4/2005 | Bauch et al. ............. 600/416 |
| 2003/0034973 A1 | * | 2/2003 | Zuiderveld .............. 345/424 |
| 2003/0219093 A1 | * | 11/2003 | Hagiwara .................. 378/4 |
| 2004/0022438 A1 | * | 2/2004 | Hibbard ................. 382/199 |
| 2004/0125908 A1 | * | 7/2004 | Cesmeli et al. ............. 378/4 |
| 2004/0264626 A1 | * | 12/2004 | Besson .................... 378/4 |

* cited by examiner

*Primary Examiner*—Xiao M Wu
*Assistant Examiner*—Abderrahim Merouan
(74) *Attorney, Agent, or Firm*—Workman Nydegger

(57) ABSTRACT

Systems and methods are provided for implementing an analytical approach to digital volumetric laminar tomography. The volumetric data visualizations generally take the form of volumetric images which approximate the spatial distribution of an x-ray attenuation coefficient throughout the region of interest in the object, such as a person, under examination. These visualizations are produced from a set of basic two dimensional data. One numerical technique employed in this regard takes the form of a process of convolution and back projection, where the convolution function is determined through the use of various analytic and empirical techniques.

55 Claims, 8 Drawing Sheets

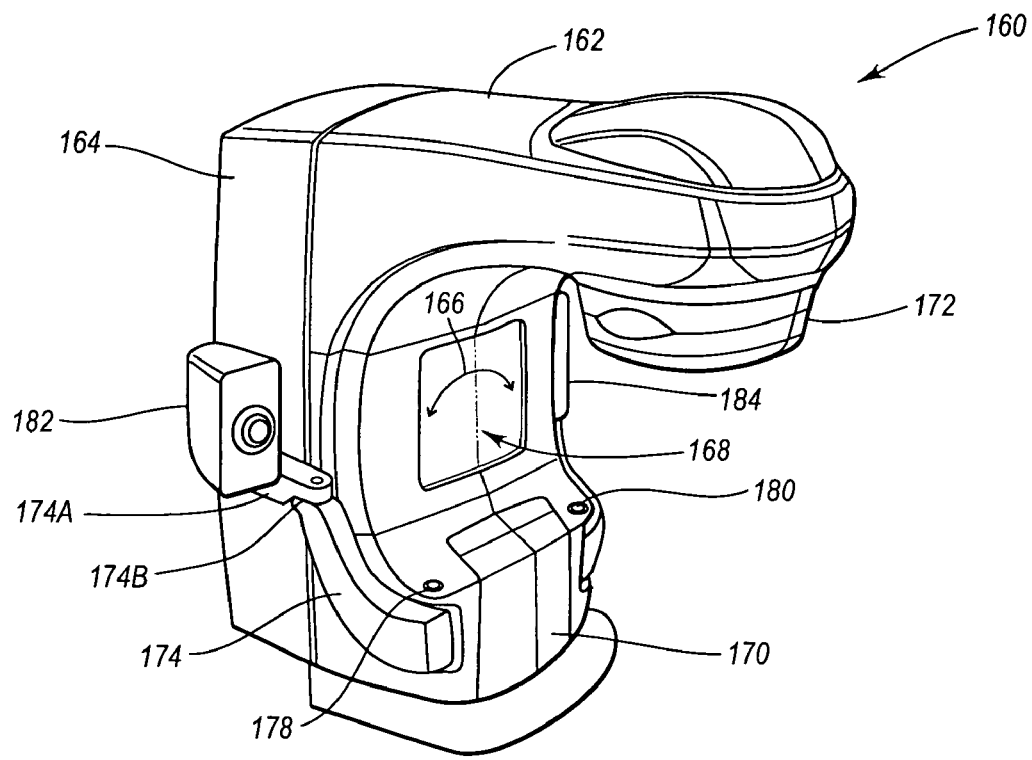
*Fig. 2A*
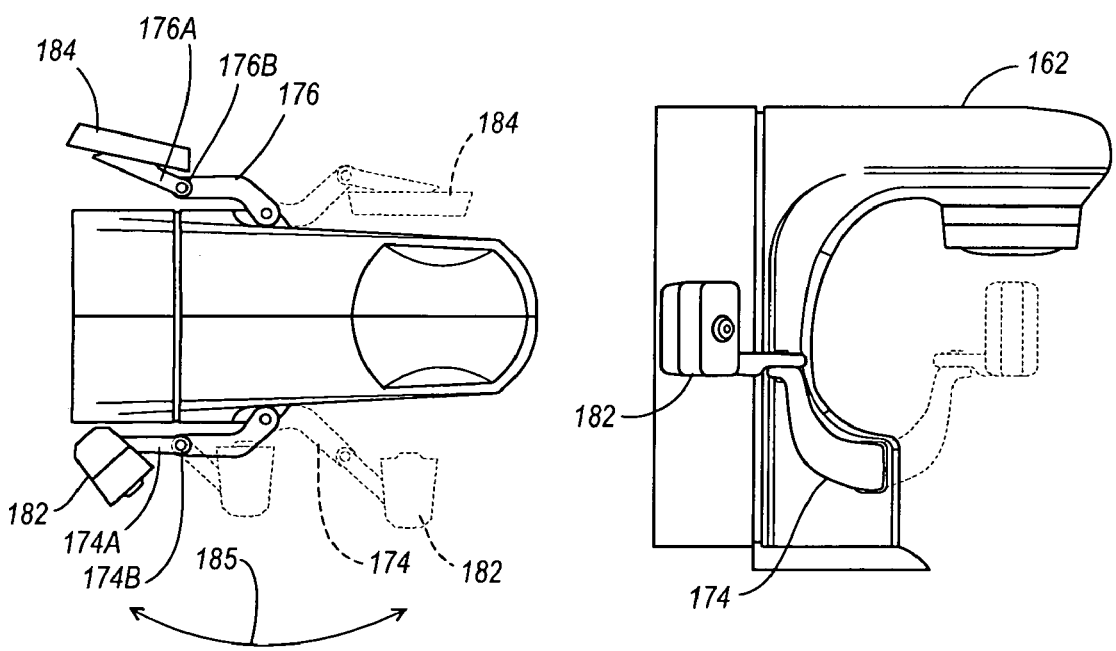
*Fig. 2B*     *Fig. 2C*

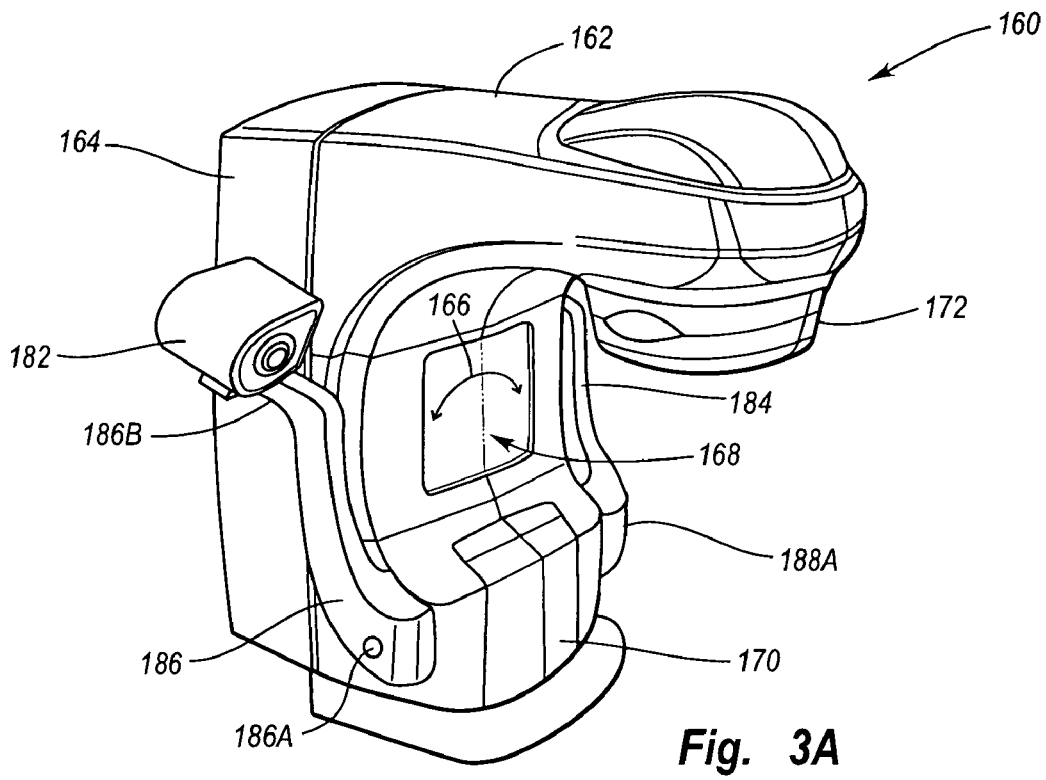
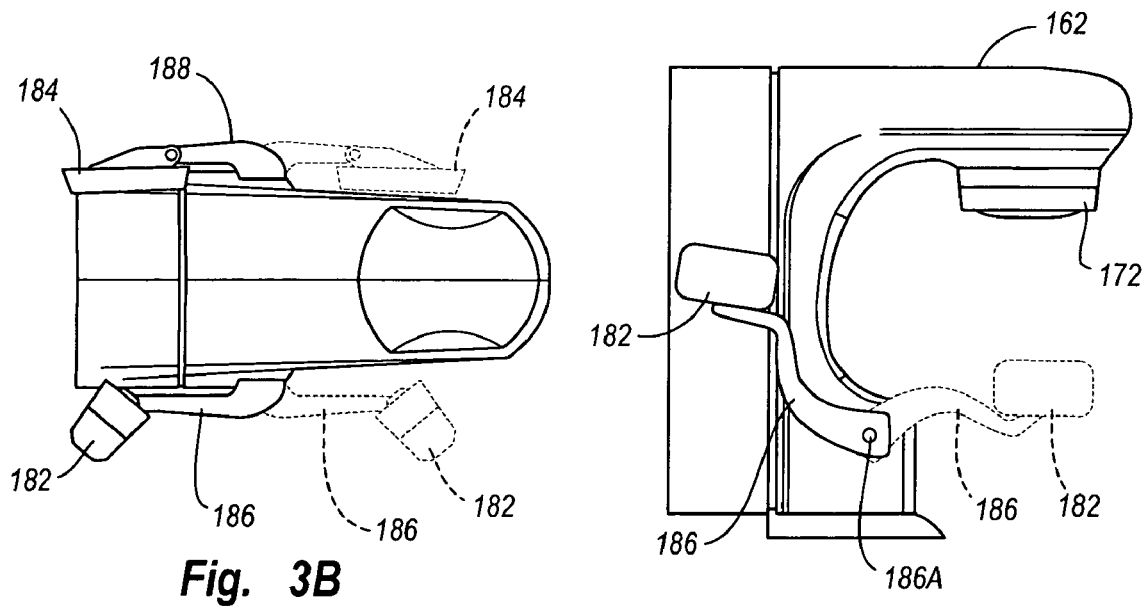
Fig. 3A
Fig. 3B
Fig. 3C

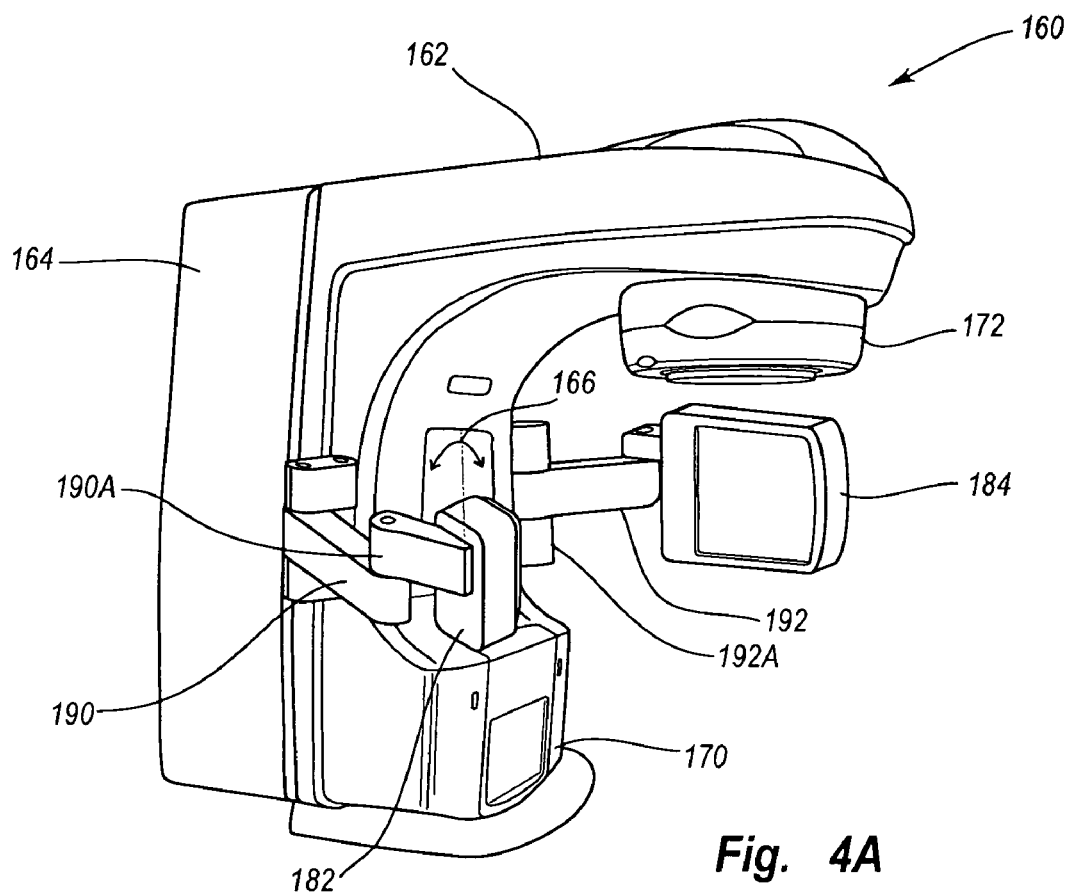
Fig. 4A
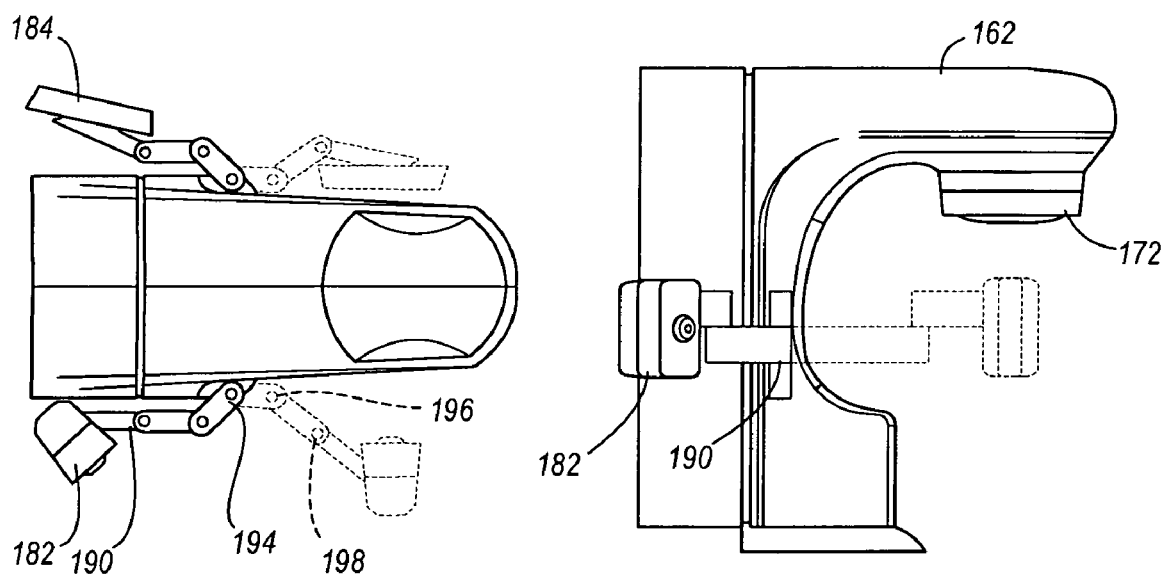
Fig. 4B  Fig. 4C

SYSTEMS AND METHODS FOR DIGITAL VOLUMETRIC LAMINAR TOMOGRAPHY

RELATED APPLICATIONS

Not applicable.

BACKGROUND OF THE INVENTION

1. Field of the Invention

The present invention relates generally to x-ray systems and devices. More particularly, exemplary embodiments of the invention concern systems and methods for using a set of two dimensional projection data to generate information that approximates x-ray behavior in a volume of interest so as to facilitate generation of tomographic images and development of diagnostic and treatment processes.

2. Related Technology

X-ray systems and devices are valuable tools that are used in a wide variety of applications, both industrial and medical. For example, such equipment is commonly used in areas such as diagnostic and therapeutic radiology. More particularly, the use of computerized tomography ("CT") for medical imaging has resulted in many advances in medical imaging, as well as diagnostic and therapeutic radiology. With respect to these particular applications, tomographic imaging has advanced from conventional, or plain film, tomography to volumetric, or helical, computerized tomography.

In what is sometimes referred to as "classical" tomography, the x-ray source and the film, sometimes referred to as a "detector," move simultaneously in opposite directions such that any line from the x-ray source to an arbitrary point on the film pivots about a fulcrum point. The motion is chosen such that the fulcrum points of lines from the source to the film surface collectively define a plane. Objects in the subject being imaged which lie close to this fulcrum, or focus plane, are in focus on the film, while objects not near this plane are blurred. This radiographic technique is also sometimes referred to as tomography, tomo, stratigraphy, and planography.

Many known tomographic processes and equipment involve the use of various numerical techniques and associated algorithms to generate and process the data necessary to radiographic procedures. For example, reconstruction algorithms based on the Radon transformation or extensions thereof are commonly employed to implement volumetric CT imaging. Other techniques sometimes employed include the algebraic reconstruction technique ("ART"), matrix inversion, and fast Fourier transform ("FFT") techniques. Moreover, such algorithms are useful for application to a variety of physical system configurations. Examples of such physical configurations include rectilinear, fan beam, "fourth generation," spiral, cone beam, multi-source, and two-dimensional detector arrangements.

While radiographic techniques such as classical tomography have proven useful and effective in many regards, problems with such techniques nonetheless remain. By way of example, practical x-ray beams, detectors and sources have finite attributes, such as their size. Moreover, the x-ray quanta are distributed in space and energy, or frequency. As well, classical tomography is prone to the presence of aliasing and other image artifacts in the generated tomographic images.

Yet another complication with typical systems and processes is that the individual detectors may have different x-ray detection efficiencies and/or nonlinear properties, depending on the intensity of the transmitted x-rays. Further, large portions of the detected x-ray intensity may be the result of scattered radiation. The detection of such scattered radiation degrades the quality, and thus the usefulness and reliability, of the generated images. Further, known systems and techniques are typically ineffectual in correcting for known systematic errors and x-ray attenuation line integrals which are optimum for the visualization. As a result, random errors often exceed acceptable limits.

In view of the foregoing, and other, problems in the art, what is needed are systems and methods configured to enable generation and accumulation of a sufficient quanta of two dimensional x-ray attenuation data such that the data has the accuracy and precision necessary to best produce the tomographic images required. Pre-processing should be applied to the data so as to correct for known systematic errors and x-ray attenuation line integrals which are optimum for the visualization. In addition, random error must be kept to an acceptable limit. Moreover, the accumulated x-ray attenuation data should reflect a set of different directions through each volume pixel, or voxel, of a volume of interest so that the voxel geometries and corresponding weights, which reflect x-ray attenuation in the respective voxels, can be used to optimize density and spatial resolution, while minimizing image artifacts, and thereby facilitate achievement of optimum visualization.

BRIEF SUMMARY OF AN EXEMPLARY EMBODIMENT OF THE INVENTION

In general, embodiments of the invention are concerned with systems and methods for using a set of two dimensional projection data to generate information that approximates x-ray behavior in a volume of interest so as to facilitate generation of tomographic images and development of diagnostic and treatment processes.

More particularly, embodiments of the invention are concerned with systems and methods for implementing an analytical approach to digital volumetric laminar tomography ("DVLT"). This approach involves the development and use of algorithms which can be used to produce visualizations of volumetric data.

The volumetric data visualizations generally take the form of volumetric images which approximate the spatial distribution of an x-ray attenuation coefficient throughout the region of interest in the object, such as a person, under examination. These visualizations are produced from a set of basic two dimensional data, specifically, data measurements of x-ray line integrals through the object. An exemplary numerical technique employed in this regard comprises a process of convolution and back projection, where the convolution function is determined through the use of various analytic and empirical techniques.

In this way, exemplary embodiments of the invention facilitate, among other things, generation of volumetric data that is useful in the development and implementation of imaging techniques, diagnostic processes, and treatment protocols. These and other, aspects of embodiments of the present invention will become more fully apparent from the following description and appended claims.

BRIEF DESCRIPTION OF THE DRAWINGS

In order that the manner in which the above-recited and other aspects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 2A through 2C represent different views of an exemplary embodiment of a radiotherapy clinical treatment machine useful in performing DVLT processes, where the radiotherapy clinical treatment machine includes an imaging device having robotic arms that swing laterally to an imaging position from a clearance position;

FIGS. 3A through 3C represent different views of an exemplary embodiment of a radiotherapy clinical treatment machine useful in performing DVLT processes, where the radiotherapy clinical treatment machine includes an imaging device having robotic arms that swing downward to an imaging position from a clearance position;

FIGS. 4A through 4C represent different views of an exemplary embodiment of a radiotherapy clinical treatment machine useful in performing DVLT processes, where the radiotherapy clinical treatment machine includes an imaging device having robotic arms that swing to an imaging position from a clearance position;

DETAILED DESCRIPTION OF SELECTED EMBODIMENTS OF THE INVENTION

Reference will now be made to the drawings to describe various aspects of exemplary embodiments of the invention. It is to be understood that the drawings are diagrammatic and schematic representations of such exemplary embodiments, and are not limiting of the present invention, nor are they necessarily drawn to scale.

I. Exemplary Digital Volumetric Laminar Tomography Apparatus

Directing particular attention now to FIGS. 1 through 8, details are provided concerning an apparatus, and associated systems and methods, for generating and gathering a set of two dimensional projection data for use in implementing digital volumetric laminar tomography processes and techniques. Generally, such two dimensional projection data can be used to generate information that approximates x-ray behavior in a volume of interest so as to facilitate generation of tomographic images and development of diagnostic and treatment processes.

Such two dimensional data projection data can be obtained, for example, by way of the apparatus 100 that is coupled to a system (not shown) for digital data collection, processing and display. Exemplary implementations of this system are configured to produce volumetric three-dimensional, as well as two-dimensional image information, that can be used in a variety of medical imaging applications.

In the illustrated implementation, the apparatus 100 includes a moveable gantry 102 upon which is mounted a two dimensional x-ray source 104 which exemplarily takes the form of an array including a multiple x-ray emitters. In some alternative implementations, the x-ray source 104 includes only a single x-ray emitter.

Disposed on the gantry 102 opposite the x-ray source 104 is a general-purpose, two-dimensional x-ray receptor 106, such as a film. As in the case of the x-ray source, the two-dimensional x-ray receptor 106 exemplarily takes the form of an array including multiple x-ray receptors but, alternatively, the two-dimensional x-ray receptor 106 may include only a single x-ray receptor.

Figure 1:
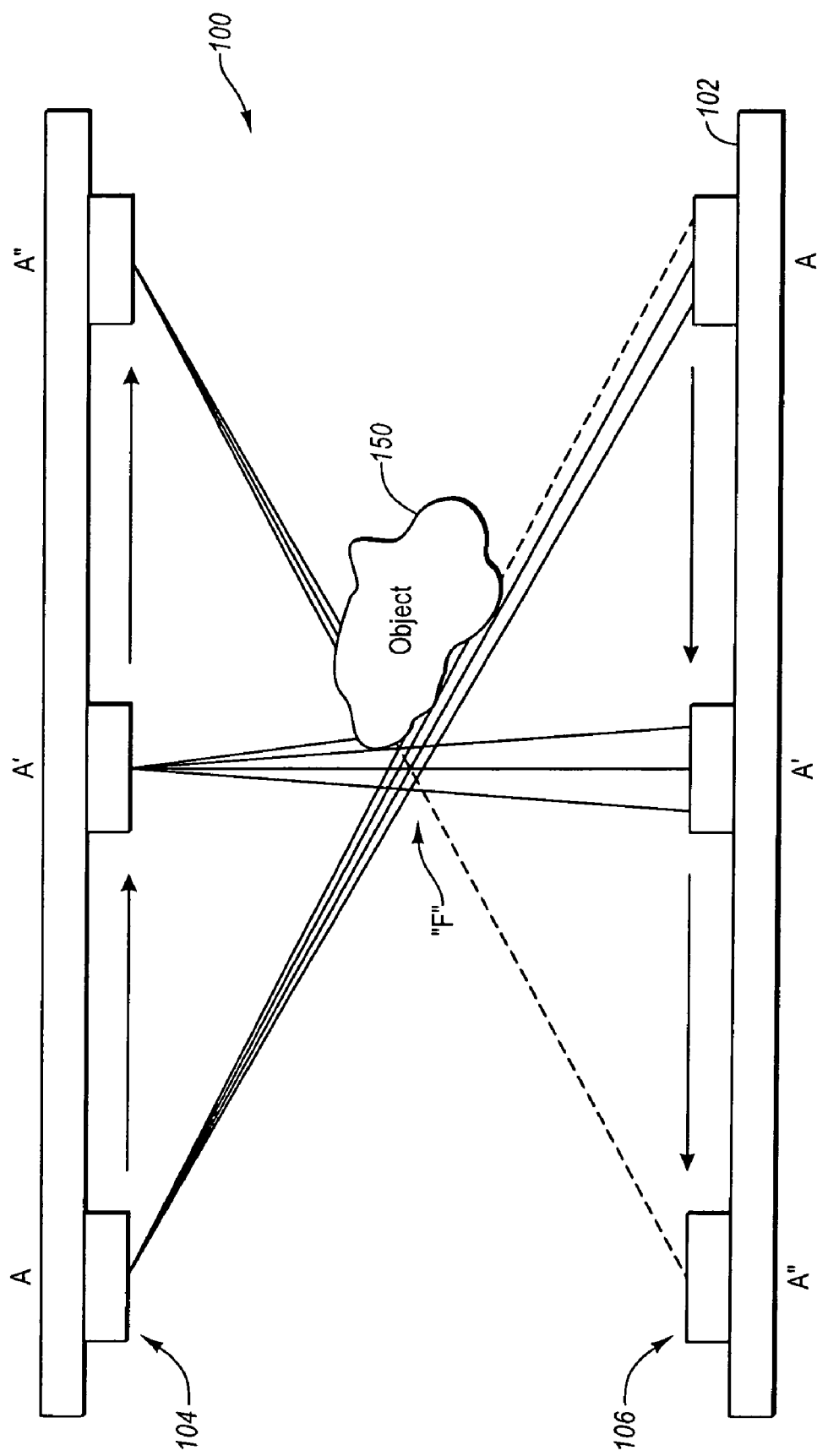
FIG. 1 is a simplified schematic diagram of an exemplary apparatus for generating and gathering projection data.

As indicated in FIG. 1, the two dimensional x-ray source 104 and the two-dimensional x-ray receptor 106 are mounted together on the gantry and are arranged for motion relative to each other so as to enable imaging of an object 150, such as the body of a patient, or portion thereof. More particularly, the two dimensional x-ray source 104 and the two-dimensional x-ray receptor 106 are arranged for linear, parallel motion relative to each other, but in opposing directions.

As a result of this arrangement, a fulcrum "F" is defined through which a straight line connecting the two dimensional x-ray source 104 and the two-dimensional x-ray receptor 106 always passes. Moreover, as the two dimensional x-ray source 104 and the two-dimensional x-ray receptor 106 move from respective A positions to A' positions, and then to A" positions, the location of the fulcrum "F" remains unchanged. In general then, the apparatus for gathering x-ray attenuation data is configured and implemented so that the location of the x-ray source traverses a two dimensional surface pattern during the course of data acquisition.

During such traverse, x-rays emitted by the two dimensional x-ray source 104 either pass by the object 150, are blocked by the object 150, or are attenuated to some extent by the object 150, the attenuation being indicated by the phantom ray lines. Generally, the extent to which the x-rays are attenuated is determined by, among other things, the density and chemical composition of the object 150. Thus, the two-dimensional x-ray receptor 106 enables the acquisition of x-ray attenuation data that is employed in various DVLT processes, as disclosed herein.

More particularly, x-ray attenuation data which has been measured at various, different, relative positions of the two-dimensional x-ray source 104, two-dimensional x-ray receptor 106, and object 150 being scanned, are required so that a suitable data set can be obtained for image construction. The motion of the two-dimensional x-ray source 104 and/or the two-dimensional x-ray receptor 106 in relation to the gantry 102, or the object 150 being imaged, may be connected or independent, but the geometrical position of each must be well known. Through the use of such two-dimensional x-ray receptors 106 and arrangements, multi-mode imaging systems can be produced.

It should be noted that while at least some exemplary embodiments of the invention are concerned with two dimensional receptor data in a certain geometry, the scope of the invention is not so limited. Rather, the systems, processes, methods and techniques disclosed herein may be implemented in a connection with a wide variety of image data acquisition geometry and hardware configurations. For example, some implementations employ two-dimensional source hardware, where the source can be characterized as single or multiple.

For example, it is not necessary for the receptor(s), or film, to view the entire volume under study each projection. Rather, the receptors can be implemented as single or multiple detector arrays. The arrays can be of arbitrary size and shape. Some exemplary geometries include single dimension geometries which may be linear or curved; two-dimensional, and planar or non planar with arbitrary shape. It should be noted that the motions of the source(s) and receptor(s) are not limited to linear or one dimensional motions. Rather, such motions can be implemented in any other way that may be consistent with desired results and functionality. For example, such alternative motions may be linear, circular, elliptical, or of any arbitrary shape. Further, such motions may be multi-dimensional in terms of their relations to space and/or time. More generally, such considerations can be applied to receptors employed in systems that employ cone, partial cone, pencil, fan, partial fan, and wide fan geometries.

In operation, an exemplary apparatus for gathering x-ray attenuation data is configured and implemented so that the location of the x-ray source traverses a two dimensional surface pattern during the course of data acquisition. In particular, and as discussed in further detail below, the attenuation data is acquired for a set of different directions through each volume pixel, or "voxel," in the volume being imaged. Further, the locations of the point source(s) and point detector(s) can be interchanged without impairing the functionality disclosed herein. Finally, the position, size, and multiplicity of x-ray sources and detectors may be adjusted as dictated by hardware considerations and physics optimization.

As suggested earlier, various configurations and arrangements of the source, detector and gantry can be employed in different combinations as necessary to meet the requirements of a particular application. In particular, the attributes of a data set will vary depending upon the image that is desired to be constructed. Thus, a data set that is useful for development of one particular image may be of little or no use in development of another, different, image. By varying the configuration and arrangement of the source, detector and gantry, data sets customized for particular images can be readily obtained.

One possible way to consider different configurations and arrangements of the source, detector and gantry is in terms of the type and extent, if any, of the motions of those components during the data acquisition process. Depending upon the configuration, one or more of the source, detector and gantry may experience linear motion, rotational motion, planar (two dimensional) motion, spatial (three dimensional) motion, and combinations of the foregoing. Such motions of a component may be determined and implemented relative to another component, or relative to a reference point or plane. The following examples of this notion are illustrative.

In one exemplary implementation, laminar tomography is performed with an x-ray device configured such that the source and detector of the x-ray device are able to move independently of the x-ray device gantry. Other laminar tomography processes are performed in connection with an x-ray device configured such that the source and/or detector of the x-ray device are rigidly mounted to the x-ray device gantry so that the source and/or detector move in unison with any motion of the gantry. In yet another exemplary laminar tomography process, the source experiences linear translational motion, while the gantry and image detector positions remain fixed. A further laminar tomography process is performed by rotating the gantry, without imparting any motion to the source or detector relative to the gantry.

Of course, the aforementioned arrangements, and those disclosed elsewhere herein, are exemplary only and the scope of the invention should not be construed to be limited to the performance of laminar tomography in connection with any particular type or configuration of apparatus. With attention now to FIGS. 2a through 4c, at least some of the aforementioned laminar tomography processes may be implemented in connection with the exemplary device illustrated there.

More particular details concerning the device disclosed in FIGS. 2a through 4c are provided in U.S. patent application Ser. No. 10/264,630, entitled AN IMAGING DEVICE FOR RADIATION TREATMENT APPLICATIONS, filed Oct. 5, 2002 and incorporated herein in its entirety by this reference. In general however, the illustrated embodiment of the radiotherapy clinical treatment machine is suitable for use in connection with performance of a variety of processes including, but not limited to, digital volumetric laminar tomography processes such as those disclosed herein.

The illustrated radiotherapy clinical treatment machine 160 includes a rotatable, or open, gantry 162 that can be pivotably attached to a drive stand 164 of the radiotherapy clinical treatment machine 160, also referred to herein simply as machine 160. The gantry 162 is capable of 360-degree rotation 166 about a centerline 168. Each gantry 162 may also include one or more radiation sources and one or more imagers. Each of FIGS. 2a through 4c show an imager 170 folded into the gantry 162 to provide more clearance. The imager 170 may be unstowed and positioned beneath the patient (not shown), or more specifically, positioned opposite a treatment radiation source 172 to provide treatment of the patient using a treatment beam, as will be described.

FIG. 2A is a perspective view illustrating one embodiment of the gantry 162 having articulating robotic arms 174 and 176, each of which is attached to a respective pivot point 178 and 180 at the base of the gantry 162. The opposite end of arm 174 is pivotally attached at a source end 174A to an imaging source 182. The opposite end of arm 176 is pivotally attached at an imaging end 176A with an imaging detector 184. For imaging, the robotic arms (174 and 176) swing outward into an adjustable imaging position along a defined trajectory 185, as shown in FIG. 2B.

In this way, the robotic arms 174 and 176 can extend and retract as necessary for positioning and clearance. In addition, the source end 174A and the imaging end 176A may include or incorporate any number of pivot points, from single plane pivots to ball joints, having 360 degrees of rotation for positioning, respectively, the imaging source 182 and imaging detector 184. In this way, the robotic arms 174 and 176 may be independently articulated into alignment for the imaging detector 184 to receive an image of the patient from the imaging source 182.

FIG. 2B is a top view and FIG. 2C is a side view of the machine 160 illustrating the swinging motion of robotic arms 174 and 176 to position the imaging source 182 and imaging detector 184 for positioning and clearance. Each arm 174 and 176 also includes respective pivot points 174B and 176B that add to the maneuverability and positioning of the corresponding arm. FIG. 2C also illustrates that each arm 174 and 176 may be curved to conform to the shape of the gantry 162 so as to maximize patient clearance.

FIG. 3A is a perspective view illustrating one embodiment of the gantry 162 having articulating robotic arms 186 and 188, each of which is attached to a respective pivot point 186A and 188A at the base of the gantry 162. The arm 186 is fixedly attached at a source end 186B to the imaging source 182. The arm 188 is pivotally attached at an imaging end 188B with the imaging detector 184. For imaging, the robotic arms 186 and 188 swing downward into an imaging position along a plane of motion, as shown in FIG. 3C.

In this way, the robotic arms 186 and 188 can extend and retract for positioning and clearance. Because the arm 186 is fixedly attached to the imaging source 182, the design is relatively simple and therefore less costly. However, in alternative embodiments, the arm 174 may be pivotally attached to the imaging source 182. In addition, the source end 186B and the imaging end 188B may include or incorporate any number of pivot points, from single plane pivots to ball joints, having 360 degrees of rotation for positioning the imaging source 182 and imaging detector 184. Therefore, the robotic arms 186 and 188 may be independently articulated into alignment for the imaging detector 184 to receive an image of the patient using the imaging source 182.

FIG. 3B is a top view and FIG. 3C is a side view of the machine 160 illustrating the swinging motion of robotic arms 186 and 188 to position the imaging source 182 and imaging detector 184 from positioning and clearance.

FIG. 4A is a perspective view illustrating one embodiment of the gantry 162 having articulating robotic arms 190 and 192, each of which is attached to a respective pivot point at a midsection of the gantry 162. The arm 190 is pivotally attached at a source end 190A to the imaging source 182. The arm 192 is pivotally attached at an imaging end 192A to an imaging detector 184.

FIG. 4B is a top view and FIG. 4C is a side view of the machine 160 illustrating the swinging motion of robotic arms 190 and 192 to position the imaging source 182 and imaging detector 184. As shown in FIG. 4B, the robotic arms 190 and 192 may each pivot at three points 194, 196, and 198 along two independent axes in a plane. For imaging, the robotic arms 190 and 192 swing outward to an adjustable imaging position, as shown in FIG. 4C.

Each pivot point 178, 180, 174B, 176B, 186A, 188A, 194, 196, and 198, can be a set of sliding mechanisms that include gears and motors that are well known to one of ordinary skill in the art. The result of such articulation can be to place the imaging detector 184 in alignment with, and at a distance from, the imaging source 182, with the target volume positioned therebetween.

Therefore, adjustments can be readily made to place the imaging detector 184 and imaging source 182 at various distances and angles from the patient by way of the articulating robotic arms 190 and 192. In this way, each of the robotic arms 190 and 192 may be positioned independently and/or in conjunction with the movement, or non-movement, and positioning of the gantry 162.

As noted earlier herein, the devices illustrated in FIGS. 2A through 4C are exemplary only, and the scope of the invention should not be construed to be limited to the devices disclosed herein. Rather, the laminar tomography processes disclosed herein may be performed in connection with any other suitable apparatus as well.

II. Aspects of Digital Volumetric Laminar Tomography

A. Applications

The use of volumetric three-dimensional, as well as two-dimensional, image information is useful in the planning and performance of procedures involving imaging with invasive diagnostic or treatment procedures. Exemplary applications for the use of such data and associated numerical techniques include, but are not limited to, surgery, oncology, angiography, image guided biopsy, and micro surgery. In addition, other applications include security applications, industrial applications, field testing, NDT (non destructive testing) applications, NDE (non destructive evaluation) applications, quality assurance techniques and the like. Further, the acquisition of high quality data sets, coupled with digital data processing and storage, enables the use of various useful imaging techniques, as well as diagnostic procedures and treatment protocols.

B. Modeling and Data Acquisition

In general, the digital volumetric laminar tomographic ("DVLT") processes, techniques and images disclosed herein are based on the acquisition of x-ray attenuation data in a set of different directions through each voxel in a volume being imaged. Such data, or data elements, obtained in connection with the systems, methods and processes of the invention comprise x-ray attenuation line integrals along rays through the object being imaged. That is, the acquired data elements correspond to the line integral of the linear x-ray coefficient along the path. In at least some implementations, the line integrals are extracted from measured x-ray intensities by simply pre-processing the acquired data by taking the logarithm of the ratio of the measured intensity with, and without, the object present. Corrections may be incorporated to account for non-logarithmic effects due to, for example, spectral effects. In this way, the apparatus is able to accumulate sufficient information having both the accuracy and precision to best produce the visualization images required.

After acquisition of the two dimensional radiation transmission data, the DVLT images are digitally generated. Many of the imaging techniques used in classical film based tomography, sometimes referred to as "x-ray stratigraphy," stereo fluoroscopy, and x-ray cineangiography, can be emulated using such techniques. In at least some implementations of the invention, the laminar images consist of views of surfaces, which may or may not be flat, through a volume of image voxels. Through digital processing, certain deficiencies inherent in film based tomography are reduced. Moreover, embodiments of the invention are also concerned with algorithms and techniques for the reduction of contrast and spatial blurring effects, and other deficiencies, often associated with conventional radiographic techniques and processes. Such reductions facilitate achievement of high quality three dimensional matrices of x-ray attenuation voxels throughout the volume.

As noted above, data acquisition processes and methods disclosed herein are performed in connection with the definition and use of voxels, or sub elements of the volume to be imaged. The term "voxel" is a shorthand notation for "volume pixel" and generally refers to a three dimensional portion of a volume of interest, such as the organ of a patient, that is to be imaged. In general, the voxels are defined to have a prescribed geometry. In some cases, the voxel geometry is substantially cubic in form. In yet other implementations however, the voxels comprise irregular hexahedrons, or other polyhedrons, where attributes such as the aspect ratio, size, and shape are selected for consistency with the information content and geometry of the x-ray transmission data to be collected.

Depending upon the requirements of a particular application or situation, the attributes of the voxel polyhedron may vary from one location to another in the volume of interest. Further, the voxel geometry and the weights can be used to optimize the density and spatial resolution, and to minimize image artifacts and thereby facilitate achievement of optimum, or improved, visualization. Of course, aspects of the overall system design can be modified to enable control of the achievable density and spatial resolution and artifact freedom of the results.

As a result of the use of a single set of two dimensional projection data to produce multiple laminar image sections throughout the volume, DVLT images often require considerably less radiation dose to produce volumetric information than typical film techniques. Moreover, the use of digital data processing and numerical analysis in connection with appropriate correction algorithms and filters enables the achievement of significant reductions in certain systematic and blurring errors which, when present, contribute to poor image quality in film tomography images.

C. Error Correction and Compensation

Although the discussion thus far has considered primarily data acquisition processes and techniques, the scope of the invention is not so limited. More particularly, in connection with such data acquisition, systems and methods are also disclosed herein for identifying and correcting, or otherwise compensating for, various errors, and for optimizing the results obtained in connection with such data acquisition. For example, it is useful in many cases to process incomplete volumetric line integral data which may contain systematic and other error, in order to determine the optimum volumetric density information for image generation, and for use in other applications such as treatment planning, patient positioning, and dose verification.

With respect to error correction, the image degradation effects from many of problem areas disclosed herein, and others, can be minimized by using a normalizing phantom and constructing difference images. In particular, degradation in image quality due to effects and conditions such as x-ray poly-chromaticity, detector spectral efficiency, detector-to-detector efficiency, non-linearity differences, and X-ray scatter, are reduced. In this procedure, the data elements are set to the difference between the measured line x-ray attenuation integral through the object of interest and the corresponding measured line integral through an object of similar attenuation but with known x-ray absorption and scattering properties.

For tissue measurements, a water or polyethylene phantom of similar volumetric shape can be used. Note also that a difference image can be produced from data sets collected during dynamic angiography studies. In this case, the normalization phantom is the patient prior to dye injection and the difference images show the time changes which result from the dye introduction. Other techniques may also be employed.

III. Numerical Analysis Techniques for DVLT

Generally, DVLT relates to a system for producing information approximating the average local x-ray attenuation coefficient of voxels throughout a volume of interest in an object, such as a patient, from a set of projection data. This information is produced for voxels in laminar surfaces in the volume of interest. However, as used herein, it will be appreciated that the term laminar is not limited to a flat or planar surface, but extends also to spherical and other geometric shapes. The information may then be viewed as laminar images or as three-dimensional images. The information can also be further processed for specialized applications such as treatment planning, patient setup, and geometrical treatment confirmation. Accordingly, the following discussion is concerned with methods for DVLT which enable generation of improved determination of volumetric imaging information.

A. Laminar Digital Construction

Attention is directed now to an algorithm for digital x-ray stratigraphy, that is, a digital emulation of classical tomography. In this approach, laminar visualizations are calculated along surfaces of interest in the object being imaged by digitally constructing views from a basic set "D" of data elements ξ. These data elements are measured values which represent x-ray attenuation line integrals along rays passing from a radiation source position through the object of interest to a detector position. In connection with the algorithm, a set "V" of voxels is defined, where each voxel represents a volume element in space, with elements v representing an attribute corresponding to the x-ray attenuation, or linear x-ray attenuation coefficient (sometimes denoted as $\mu$), in a voxel. Generally, the linear x-ray attenuation coefficient is defined as the probability, per unit path length traveled, that an x-ray photon will interact with the material through which it passes.

By definition, a non zero subset "A" of data points exists for any voxel of interest in the object, where each data point in the subset satisfies the proposition $\pi_A(\xi)$ that the geometrical line from the center of the x-ray source element to the center of the detector element passes through the voxel volume. Symbolically, "A"=$\{\xi:\pi_A(\xi)\}$.

Additionally, a subset of voxels of interest "I" is defined where "I"=$\{v:v_1(v)\}$ and which satisfy the proposition $v_1$ that the voxel is on a surface where a visualization image is required. A stratigraphic image approximation to the values of v is simply a normalized sum of ξ in "A" for each of the v in "I." In some cases, the normalizing factor is simply the inverse of the number of ξ summed. Further improvements in results may be obtained, in at least some cases, by using an appropriate algorithm to assign appropriate weights κ to the elements in the sum determining v. The aforementioned evaluation of "I" can be represented as the following function (where "j" is the voxel number):

$$v_j(\xi \in A_j) = \sum_{\xi \in A_j} K_p \xi_p. \qquad \text{EQ. 1}$$

Various other algorithms may be suitable as well however. Accordingly, the scope of the invention should not be construed to be limited to the aforementioned algorithm.

The elements v in "I" can be appropriately indexed and viewed or analyzed as an approximate x-ray image of the object at the surface defined by $v_1(\ )$. This is similar to using classical tomography to generate a film tomogram of the laminar surface. In either case, the pattern of material in the focal plane tends to show sharp spatial resolution and there are blurring and other artifacts due to material in the object which is out of the focal lamina. By defining the details of the data collection system and the associated geometry, the propositions $\pi(\ )$ and $v(\ )$ and the sum weights κ with appropriate normalization, most, if not all, of the current techniques of film stratigraphy can be emulated. For one example stratigraphy exposure, film stratigraphy typically produces a reduced blur image along only one surface in the object being imaged. Digital processing of data from one exposure typically allows production of reduced blur surfaces throughout the volume of the object. The reduced blurring image can be produced from a single measurement set. The digital processing further allows for production of volume images simulating no blurring. Further, generation of images based on new algorithms for stratigraphy can also be developed. By way of example, images may be generated that emulate results that would be obtained from a combination of linear, helical, cycloidal, hypocycloidal, circular and other classical tomographic techniques. Also, since images of multiple laminar surfaces can be produced from a single data set, dose reduction or, conversely, image improvement, can be achieved.

With respect to the foregoing, it was noted earlier herein that classical tomography is susceptible to the presence of certain image artifacts that degrade the quality of the obtained image. Nonetheless, the use of an ideal or optimum proposition $\pi(\ )$ and the related weights κ has various useful effects on the quality of the resulting digital images.

For example, $\pi(\ )$ is defined, in at least some cases, to represent the proposition that for each data point in the subset, the geometrical line from the center of the x-ray source element to the center of the detector element passes through the cross section of the voxel in the plane defined by the center points of neighboring voxels. The weights may be determined, for example, with reference to the perpendicular distance from the center of the voxel to the source to the center of the x-ray source element.

Alternatively, $\pi_A(\xi)$ is defined, in at least some cases, to represent the proposition that for each data point in the subset, the geometrical line from the center of the x-ray source element to the center of the detector element passes through the cross section of the voxel, or an adjacent voxel in the plane defined by the center points of neighboring voxels. As in the previous example, weights must be appropriately defined and assigned. Of course, a variety of different propositions $\pi_A(\xi)$ may be defined and employed as well.

The set of voxels "V" with elements v is itself a subset of the set of all possible voxel definitions. Moreover, the set of voxels "V" with elements v is based on a proposition $\zeta_V()$ defining, for example, the shape of an irregular hexahedron voxel optimum for the mathematical model of the system. As noted above, the geometry and volume of the voxels need not be constant throughout the object to be imaged. As in the case of the proposition $\pi_A(\xi)$, a variety of different propositions $\zeta_V()$ may alternatively be defined and employed. The particular proposition selected, in turn, affects the choice of $\pi()$ and the corresponding weights $\kappa$.

Choices such as those described above are typically constrained by the particular specifications for the attributes of the image, such as the voxel attribute desired, the required spatial resolution, and limitations of the data, such as completeness and accuracy. Other considerations inform those choices as well. At least some of such considerations relate to the potential for errors in the acquired data.

As suggested elsewhere herein, in DVLT imaging the acquired data be accurate and substantially free of uncorrectable systematic errors, although some random error is generally always present in the data. However, imaging algorithms can, in some cases, introduce new errors and/or further amplify existing errors. Thus, due consideration of the potential for such errors, which typically appear in the image as poor density, poor spatial resolution or artifacts, should be given in the design of the data acquisition system, as well as in the design of algorithms for image production and processing.

The above considerations on digital stratigraphy are related as well to the matrix approach to tomography. In one implementation of the matrix approach, an index "i" is assigned to each of the data points (x-ray line integral) elements $\xi_i$ to form a vector $\xi$, and an index "j" is assigned to each of the voxels $v_j$ to form a vector v. Next, a determination is made of a weight $\omega_{ji}$ such that $\omega_{ji} * v_j$ is the x-ray line integral through the voxel "j" for the x-ray ray from the center of the source to the center of the detector for the data element $\xi_i$.

Note that for most imaging systems, many of the $\omega_{ji}$ are zero. It is also known that $\xi = \omega * v$. Thus, the image reconstruction problem may be considered to be the inversion of this matrix equation. Note, as well, that if $i=1 \ldots, I$ and $j=1 \ldots, J$, the number of data points I is not necessarily equal to the number of voxels J, though I may be equal to J in some instances. In general however, $I \neq J$.

In order to precisely determine the voxel values, there must be J independent equations. Exemplary implementations of the reconstruction algorithm perform a least square type of solution of the equations to generate an image which "best" fits the data. Depending on the particular definition of "best" fit, a family of "acceptable" images can be generated from a single data set. The quality of the reconstructed image depends upon, among other things, the accuracy with which the matrix models the physical conditions, the degree of ill condition of the matrix, and the quality of the data. In general, computerized tomography image reconstruction techniques produce images which can be viewed as some form of the least square approach, or vice versa.

In application, the data contained in $\xi$ can be viewed in a variety of ways. In computerized tomography, the voxel values v are determined and then viewed as planar images corresponding to planes passing through the object being imaged. Digitally reconstructed radiographs can be formed by, for example, summing the voxels in v along divergent rays from a point x-ray source to image to form a shadow gram, a digital radiographic image equivalent to a standard x-ray radiographic film image. Of course, the shadow gram can often be obtained without reconstruction by applying an appropriate algorithm directly to the data. As discussed above, stratigraphic or classical tomographic images can also be obtained from the data. In this way, the data viewed by the observer is tailored to optimize useful information transfer for the particular application.

B. Iterative Process for DVLT

Figure 5:
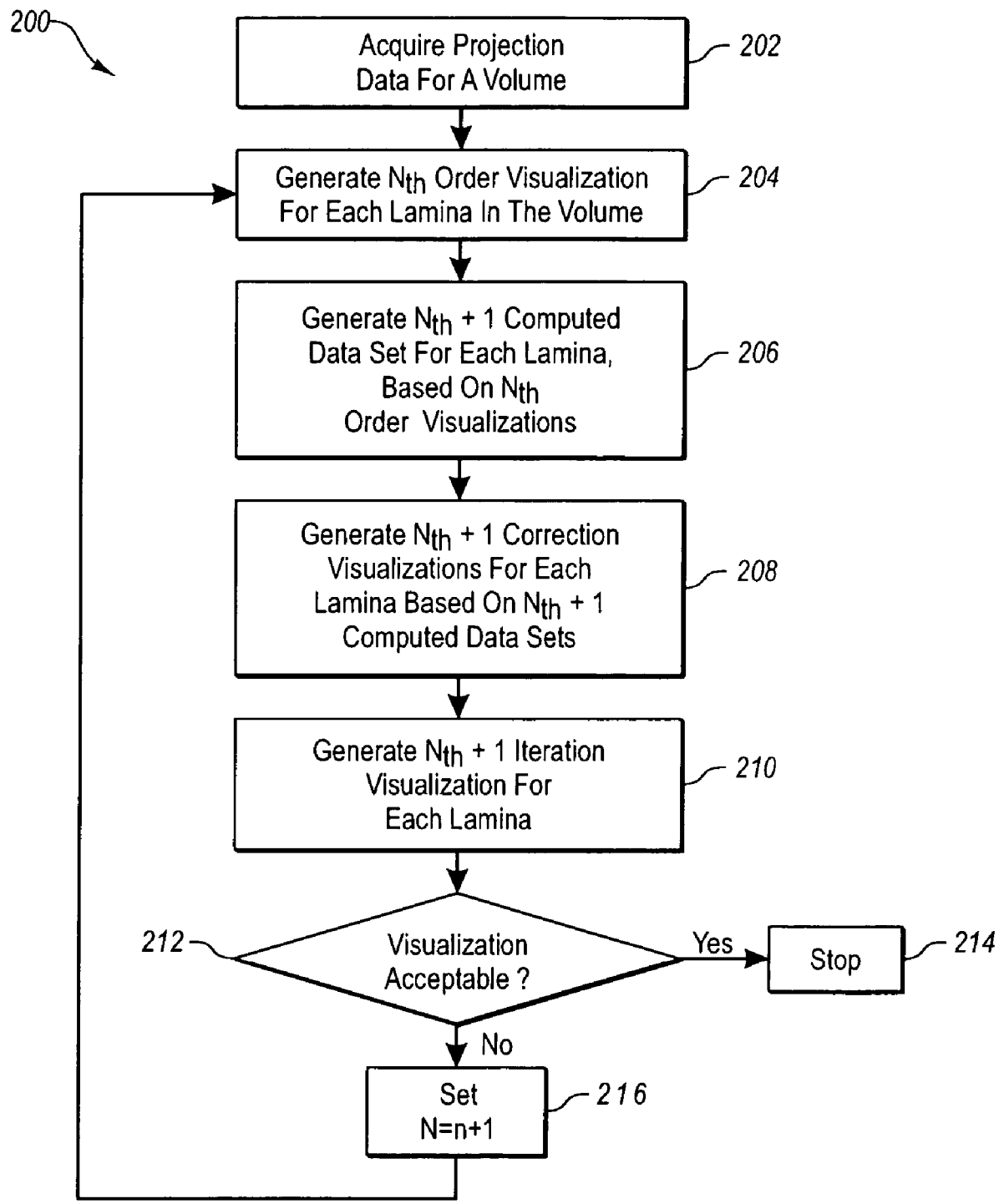
FIG. 5 is a flow diagram illustrating aspects of an exemplary process for generating a DVLT image.

Attention is directed now to an algorithm for DVLT, exemplified by process 200 of FIG. 5, which aids the visualization by reducing the blurring in contrast and spatial resolution often present in classical tomography. In addition to classical tomography, DVLT also allows for the production of reduced blurred volume images. In general, the use of the algorithm and other related algorithms and procedures results in a visualization which more nearly approximates a visualization of the x-ray attenuation coefficients of voxels in the object being scanned.

Based on the concepts disclosed elsewhere herein, a family of sets of voxels of interest $I_k$ is defined which represents layered surfaces of interest throughout the volume of the object being visualized. Generally, the algorithm involves the use of the known data values in the basic data set denoted as $D^{<0>}$, gathered at stage 202 of the process, to determine values of the elements v in "I" optimized for use in image visualization or in other applications requiring volumetric x-ray attenuation data for analysis. It should be noted that the sets $I_k$ must be defined to conform with certain requirements for the application of algorithm to be described. These include requirements imposed by "layering," and in set notation the intersection $I_k \cap I_l$=null if l is not equal to k. Other restrictions may apply as well.

With the foregoing in view, attention is directed now to various stages of an exemplary algorithm sequence. After the data has been acquired, the process advances to stage 204 where the acquired data is used to generate a $0^{th}$ order visualization set $I^{<0>}$ for each layer or lamina in the volume to be imaged. More particularly, this stage consists of using the algorithm disclosed above in A. Laminar Digital Construction to evaluate all of the elements in all $I_k$. This stage may also be referred to as the $0^{th}$ evaluation and the result of the stage denoted $I_k^{<0>}$, where the union of the $I_k^{<0>}$ is indicated as $I^{<0>}$. Thus, $$v_j(\xi \in A_j) = \sum_{\xi \in A_j} K_p \xi_p. \qquad \text{EQ. 2}$$

becomes:

$$v_j^{<0>}(\xi^{<0>} \in A_j) = \sum_{\xi_p^{<0>} \in A_j} K_p \xi_p^{<0>} \qquad \text{EQ. 3}$$

where "A"=$\{\xi:\pi_A(\xi)\}$. This evaluation produces digital images substantially equivalent to classical tomography for each layer in the object.

In the next stage 206 of the algorithm sequence of process 200, the first iteration visualization results, less one voxel lamina layer, are used to produce a first iteration calculated data set for each missing layer. That is, $I^{<0>}$ is used to generate computed data set $D^{<1>}$.

More particularly, the data elements in the basic measured data set $D^{<0>}$ correspond to some function of the x-ray attenuation properties along the beam from the source to a detector. The measurement data are the result of measurement with a system having a set of physical attributes associated with each data element. For each data element in $D^{<0>}$, a set $B_i$ of voxels is selected which satisfies the proposition $\mu_B(v^{<0>})$ that the line from the center of the source to the center of the detector for a particular element passes through the perpendicular cross section of the voxel, where "i" is a number assigned to the data point.

Symbolically, $$B_i = \{v^{<0>}, \mu_B(v^{<0>})\}, \text{ and } C_{im} = B_i - I_m. \quad \text{EQ. 4}$$

Thus, a computed data set $$D^{<1>}_m = \{\xi_1^{<1>}, \xi_2^{<1>}, \xi_3^{<1>}, \ldots\}_m \text{ is formed,} \quad \text{EQ. 5}$$

the $i^{th}$ element of which is determined from the equation (where $\omega_p$ is a weighting factor):

$$\xi_i^{<1>}(v^{<0>} \in C_{im}) = \sum_{v_p^{<0>} \in C_{im}} \omega_p v_p^{<0>}. \quad \text{EQ. 6}$$

In at least some applications, it is useful to set $\omega_p$ equal to the reciprocal of the number of elements in $B_j$. In general however, the value of $\omega_p$ should be based on a model which best approximates the physical attributes of the particular measurement system employed. By employing the method as described above in the determination of $I_m^{<0>}$, but using $D_m^{<0>}$ instead of $D^{<0>}$, a correction visualization is determined, at stage 208, that is subtracted from $I_m^{<0>}$ to obtain $I_m^{<1>}$. Also, to improve convergence of the iterative process the correction to $I_m^{<0>}$ may be multiplied by convergence factor before subtracting from $I_m^{<0>}$ in particular not including the convergence factor.

$$v_j^{<1>}(\xi^{<1>} \in A_j) = v_j^{<0>} - \sum_{\xi_p^{<1>} \in A_j} K_p \xi_p^{<1>}. \quad \text{EQ. 7}$$

Where $A = \{\xi : \pi_A(\xi)\}$,
and for $v_j \in I_m$ (which determines m), $$\xi_i^{<1>}(v^{<0>} \in C_{im}) = \sum_{v_p^{<0>} \in C_{im}} \omega_p v_p^{<0>}$$

where $C_{im} = B_i - I_m$ $B_i = \{v^{<0>}, \pi_B(v^{<0>})\}$.

After the iteration visualization is generated at stage 210, this process 200 can be repeated as necessary to determine iterated visualizations. If, at stage 212, the visualization is deemed acceptable or otherwise in conformance with established criteria, the process terminates at stage 214. On the other hand, if further iterations are desired, the process advances to stage 216 and, ultimately, back to stage 204, where the next visualization is initialized. More particularly, the succeeding visualization n+1 is obtained from the $n^{th}$ visualization by applying the algorithm:

$$v_j^{<n>}(\xi^{<n>} \in A_j) = v_j^{<0>} - \sum_{\xi_p^{<n>} \in A_j} K_p \xi_p^{<n>}. \quad \text{EQ. 8}$$

Where $A = \{\xi : \pi_A(\xi)\}$,
and for $v_j \in I_m$ (which determines m), $$\xi_i^{<n>}(v^{<n-1>} \in C_{im}) = \sum_{v_p^{<n-1>} \in C_{im}} \omega_p v_p^{<n-1>}$$

where $C_{im} = B_i - I_m$ $B_i = \{v^{<0>}, \pi_B(v^{<0>})\}$.

A measure of the applicability of the process is the quality of the final visualization. Generally, this image quality is determined by considerations such as the optimization of weights $\kappa$ and $\omega$, the optimization of the definition of the voxel sizes and shapes, and the quality, precision, and accuracy of the data. In at least some cases, the difference vector $\delta_j^{<n>}$ in correction quantities for succeeding iterations, $$\delta_j^{<n>} = \sum_{\xi_p^{<n>} \in A_j} K_p \xi_p^{<n>} - \sum_{\xi_p^{<n+1>} \in A_j} K_p \xi_p^{<n+1>} \quad \text{EQ. 9}$$

should converge to zero. The use of a least square type of approach, which varies the weights of voxel attributes to minimize this difference, produces improved results in some cases. More generally, the choice of algorithms or parameter values will be guided by the requirements of a particular situation so that systematic convergence to negligible quantities can be achieved while, at the same time, undesirable oscillation of the difference vector is largely avoided. In some cases, the introduction of suitable convergence factors in the iterative process contributes to a reduction in difference vector oscillations. For example, the use of the convergence factor for this least squared process can simplify the least squared processing.

To briefly summarize then, an exemplary implementation of an iterative process for DVLT involves a number of stages. Initially, the collected data set is used to yield a $0^{th}$ visualization, one for each layer or lamina in the volume to be imaged. Next, the first iteration visualization results, excluding one voxel lamina layer, are used to produce first iteration calculated data sets, one calculated data set for each missing layer. Then, the calculated data sets are used to produce first iteration missing lamina correction visualizations for each layer. At the next stage of the process, the first iteration visualization for each lamina, one for each layer, is produced by subtracting the first order missing correction visualization, or an appropriate fraction thereof, from the $0^{th}$ visualization for each layer. The process is continued by determining a second iteration calculated data set from the first iteration visualization, generally as described above. The second data set, in turn, is used to determine a second iteration correction visualization. And from this a second iteration visualization is determined by subtracting the second iteration correction visualization from the $0^{th}$ visualization. The process can then be continued until the desired image visualization is produced.

With respect to the foregoing, and other algorithms and sub-algorithms, disclosed herein, various alternatives remain in the detail application and optimization of each sub-algorithm. These choices of particular alternatives may have a substantial effect on both the success of the algorithm and the quality of the result and should, accordingly, be selected to be consistent with a particular application and desired result.

Thus, alternative iterative process stages may be defined and employed in certain situations. As one example, instead of correcting the $0^{th}$ visualization, it may be useful in some cases to develop a basic algorithm directed to correction of the collected data set so as to aid development of computed data sets which correspond to the data set that would be observed if only the laminar surface of interest were present in the object being scanned. These would be visualization sets of laminar surfaces in the object of interest. Such alternative basic algorithms can advance the understanding of how the various parameters and empirical portions of the data analysis can be developed to optimize the results. To the extent that the processes are linear, the results obtained with the processes will reflect that. Further, the function and weights as defined above are linear as well. However, differences which can be introduced in the definition of the various sets above introduce non-linearity. The iterative approach may be combined with the convolution approach (discussed below) to generate a reconstruction algorithm which contains a sub algorithm which combines iterative and convolution DVLT.

IV. Convolution Approach to Digital Volumetric Laminar Tomography

Figure 6:
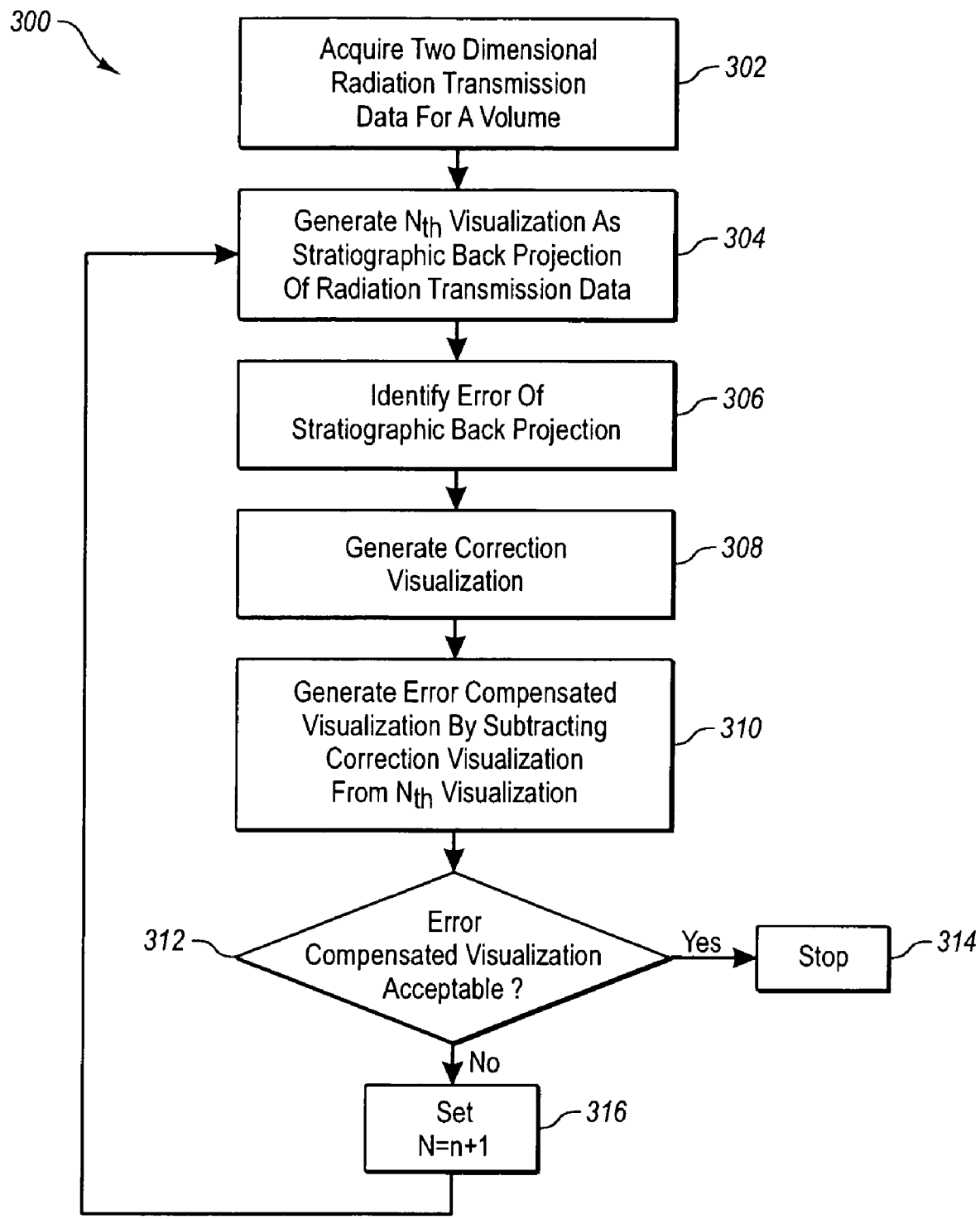
FIG. 6 is a flow diagram illustrating aspects of an alternative process for generating a DVLT image.

Attention is directed now to methods, processes and algorithms for implementing a convolution type approach to DVLT, one example of which is illustrated in FIG. 6 as process 300. In this type of approach, data is collected at stage 302 and the iteration represented by the following equation 8, discussed above:

$$v_j^{<n>}(\xi^{<n>} \in A_j) = v_j^{<0>} - \sum_{\xi_p^{<n>} \in A_j} K_p \xi_p^{<n>}.$$

Where $A = \{\xi : \pi_A(\xi)\}$,
and for $v_j \in I_m$ (which determines m), $$\xi_i^{<n>}(v^{<n-1>} \in C_{im}) = \sum_{v_p^{<n-1>} \in C_{im}} \omega_p v_p^{<n-1>}$$

where $C_{im} = B_i - I_m$ $B_i = \{v^{<0>}, \mu_B(v^{<0>})\}.$ is considered to be a form of convolution back projection, where the elements of the image represented by the first term on the left hand side constitute a stratiographic back projection of the data, generated at stage 304. The error of the stratiographic back projection is identified at stage 306 and a corresponding correction visualization generated at stage 308. At stage 310, the error of the stratiographic back projection is compensated by subtraction of the correction image. Similar to the case of the algorithm illustrated in FIG. 5, a determination is made at stage 312 as to whether the resulting error compensated visualization is acceptable or otherwise meets established criteria. If so, the process terminates at stage 314. If further iterations are desired, the process advances to stage 316 and, ultimately, back to stage 304, where the next visualization is initialized.

With more particular reference to the correction image noted above, the elements of the correction image are determined by the second (negative) term in the foregoing equation. This correction image can be regarded as a back projection of a convolution of the data with a convolution function characterized by convolution weights $\gamma_p$. Thus, the reconstruction problem reduces to the determination of these $\gamma_p$ coefficients.

In general, the weights $\gamma_p$ are determined and optimized for the geometry and attributes of the detection system, the characteristics of the data set for each mode of data collection by the system, and the requirements and attributes of the visualizations required, for example, the desired lamina and voxel characteristics. With respect to convolution, the following equation should be considered:

$$\rho_j(\xi \varepsilon D_j) = \sum_{\xi_p \varepsilon D_j} \gamma_p \cdot \xi_p$$

where, $D = \{\xi : \psi_D(\xi)\}$

For digital convolution, $\xi_p$ are data points, $\rho_p$ are the convolved data points, j and p are indices in data space and $\gamma_p$ are the weights noted above. Further, D is the set of $\xi$ which satisfy the proposition $\psi_D(\xi)$ that $\gamma_p$ not zero for D.

With respect to back projection, the following is considered:

$$v_j(\xi \varepsilon A_j) = \sum_{pm \varepsilon A_j} \rho_m$$

where, $A = \{\xi : \pi_D(\xi)\}$

As discussed below, various analytical techniques are used in connection with the algorithms discussed earlier to estimate the values of the coefficients $\gamma_p$, given the coefficients $\omega_p$ and $\kappa_p$. Additionally, various empirical techniques are used to experimentally calibrate an imaging system and thereby facilitate determination of a set of convolution coefficients $\gamma_p$ to be applied for image reconstruction.

Figure 8:
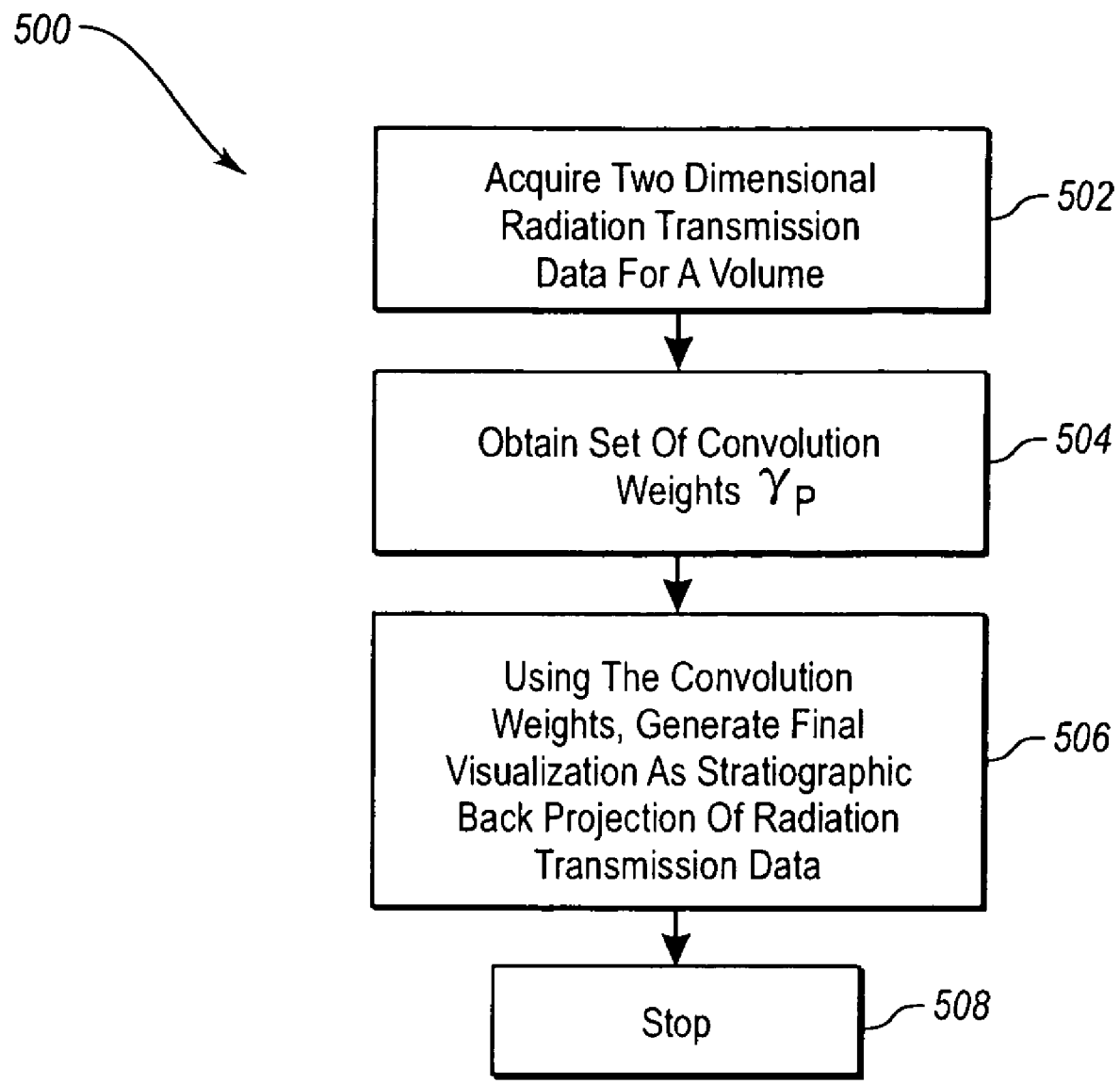
FIG. 8 is a flow diagram illustrating aspects of a non-iterative process for generating a DVLT image based upon a set of convolution coefficients.

As discussed in further detail below in connection with FIG. 8, once a set of coefficients $\gamma_p$ have been determined, whether computationally or empirically, for at least some objects, only one reconstruction convolution and back projection operation is necessary to produce an acceptable visualization. In such cases, no iterative process is employed. With attention now to component visualizations, the following sections describe methods for determining the $\gamma_p$ from calibration data using phantoms, and from theory using the iterative technique. Methods for the combination of the two techniques for application are also disclosed.

A. Algebra of Component Visualizations

The first portion of the convolution approach to DVLT involves a consideration of the algebra of the visualization components where, among other things, it is shown that visualizations can be considered as composed of linear components. More particularly, for the formulation of a convolution approach in terms of subtraction of a scaled correction image, use is made of the linearity of the various elements in the system. As discussed below, this correction image can be considered to be made up of a linear sum of component correction images. Additionally, the data elements are line integrals, as discussed earlier, and it should be noted that in the iteration algorithm, reconstructed images are linear in the data elements, and the various visualization images are both linear and additive.

For example, the following equation can be written, in terms representing various visualizations:

$$^{cor}I_m = {}^{bkp}I_m - {}^{\Delta}I_m \qquad \text{EQ. 10}$$

where, for the $m^{th}$ lamina, $^{cor}I_m$, $^{bkp}I_m$ and $^{\Delta}I_m$ represent the indexed visualization sets, specifically, $I_m = \{v_1, v_2, v_3, v_4 \ldots\}$, for the correct, or reconstructed, image, the $0^{th}$ visualization being constructed by back projection. The foregoing represents one exemplary formulation for the determination of the correction image. Below, the correction image $^{\Delta}I_m = \{\Delta_1, \Delta_2, \Delta_3, \Delta_4 \ldots\}$ is expanded in terms of the data elements of the basic data set, and an analytic approach to the determination of the convolution coefficients, discussed above, is developed. Here, $^{\Delta}I_m$ may also be expressed as $^{bkp}\Delta I_m$.

B. Analytic Iterative Approach to Determination of Coefficients $\gamma_p$

An analytic iterative approach is now presented for the determination of the convolution coefficients $\gamma_p$. Aspects of an empirical approach which involves an experimental method for system calibration are presented elsewhere herein.

Initially, consideration is given to the nth correction image $\Delta_j^{<n>m}$ for $n > 1$:

$$\Delta_j^{<n>m} = \sum_{\xi_p^{<n>m} \in A_j} K_p \xi_p^{<n>m} \qquad \text{EQ. 11}$$

$$= \sum_{\xi_p^{<n>m} \in A_j} K_p \sum_{v_q^{<0>} \in C_{pm}} \omega_q \left[ v_p^{<0>} - \sum_{\xi_k^{<n-1>m} \in A_p} K_k \xi_k^{<n-1>m} \right]$$

$$\Delta_j^{<n>m} = \sum_{\xi_p^{<n>m} \in A_j} K_p \xi_p^{<n>m} \qquad \text{EQ. 12}$$

$$= \sum_{\xi_p^{<n>m} \in A_j} K_p \sum_{v_q^{<0>} \in C_{pm}} \omega_q \left[ \sum_{\xi_k^{<0>} \in A_p} K_k \xi_k^{<0>} - \sum_{\xi_k^{<n-1>m} \in A_p} K_k \xi_k^{<n-1>m} \right]$$

The foregoing equations give the correction image for the $(n+1)^{th}$ visualization in terms of the data sets $D^{<0>}$ and $D^{<n-1>}$. If $n=1$ is set, the foregoing equations give the correction image for the second visualization iteration in terms of the basic data set $D^{<0>}$. The correction image for the third visualization iteration in terms of the basic set $0 <0>$ can be obtained by noting that the last term in the preceding equations:

$$\sum_{\xi_k^{<n-1>m} \in A_p} K_k \xi_k^{<n-1>m} \qquad \text{EQ. 13}$$

is $\Delta_p^{<n-1>m}$. An expression for $\Delta_p^{<n-1>m}$ can be obtained by replacing "n" by "n−1" and "j" by "p" in $\Delta_j^{<n>m}$ and substituting the result for [the last term of equation 4.2]. This gives the correction image for the $(n+1)^{th}$ visualization in terms of the data sets $D^{<0>}$ and $D^{<n-2>}$. If $n=2$ is now set, the correction image for the third visualization iteration is obtained in terms of the basic data set $D^{<0>}$. This process can be continued to obtain an expression for the correction image for the $(n+q)^{th}$ visualization in terms of the data sets $D^{<0>}$ and $D^{<n-q+1>}$.

Earlier, it was noted that the correction image can be regarded as a back projection of a convolution of the data with a convolution function characterized by convolution weights, or coefficients, $\gamma_p$. The expression for the correction image for the $(n+q)^{th}$ visualization is a sum over the elements of the data set $D^{<0>}$ with coefficients determined by sums over products of the ω and κ weights. These sums are analytical expressions for the convolution weights $\gamma_p$.

Note also that as iterations advance to succeeding orders of the correction image, more of the data elements from $D^{<0>}$ have non-zero coefficients. However, it should also be noted that on succeeding iterations, the additive term in the sums is a higher order product of the ω and κ weights. To the extent that the ω and κ weights are fractional, the contribution from changes to terms of data elements with non zero coefficients and from the addition of data elements which previously had a zero coefficients, are successively smaller with each successive iteration.

In typical CT reconstruction, the convolution function is carried to very large q. For large q, the difference in succeeding iterations of the correction image should be relatively small. The terms of the last term in EQ. 12 differences from the $n^{th}$ computed data sets $D^{<n+q>}$ and $D^{<n+q+1>}$ in the correction image may be negligible. The success of this technique is at least partially dependent upon the conditioning of the system of equations, and the rapidity of convergence. Thus, the technique should reflect a balance between image quality on the one hand, and errors due to a failure to carry an insufficient number of terms, on the other hand.

C. Empirical Approach to Correction Visualization

Figure 7:
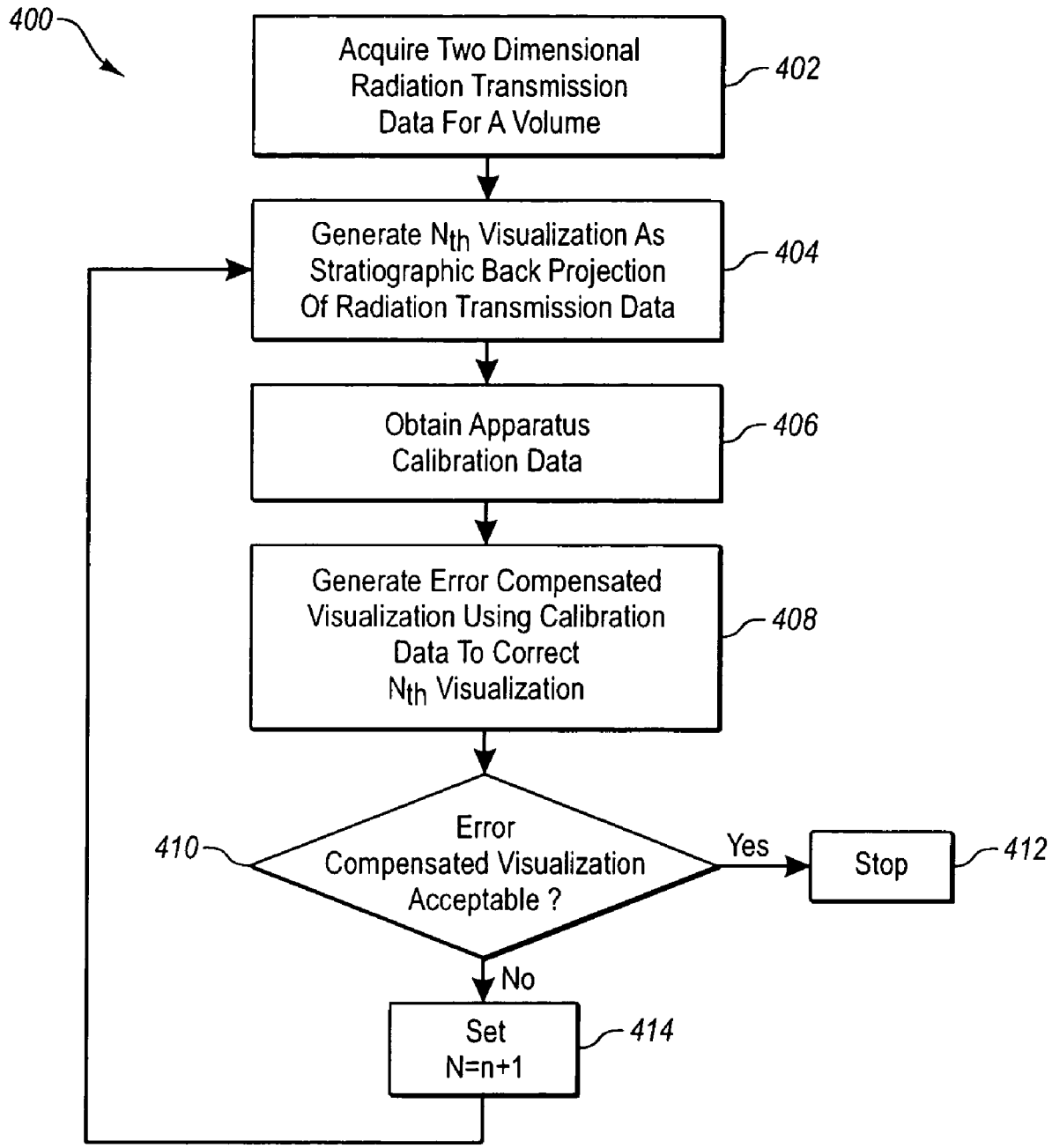
FIG. 7 is a flow diagram illustrating aspects of yet another alternative process for generating a DVLT image.

The following describes an empirical approach to correction visualization and is illustrated as process 400 in FIG. 7. Briefly summarized, at stage 402, two dimensional radiation transmission data is obtained and, at stage 404, a visualization is generated as a stratiographic back projection of the transmission data. Proceeding to stage 406, calibration data is obtained from the hardware system or apparatus to be used for DVLT. This calibration data is then processed to obtain general point response correction visualizations which can be used in the DVLT algorithm to produce corrected visualizations, as indicated at stage 408. At stage 410, a determination is made as to whether the error compensated visualization meets various predetermined criteria. If the criteria are satisfied, the process 400 terminates at stage 412. If further iterations are desired, the process advances to stage 414 and, ultimately, to stage 404.

While one specific implementation of this approach is discussed below, it should be noted that the concepts discussed can be formulated in a variety of ways and the scope of the invention should not be construed to be limited to any particular implementation.

With more particular reference now to the process 400, the calibration procedure consists of acquisition of point response data sets using specially designed phantoms for calibration imaging. The simplest calibration phantom consists of a single small point x-ray absorber. The size of the point is such that when viewed from any geometry used in data set data collection, the cross sectional area is within the boundaries of the polyhedron visualization voxels for one, two, or more of the projections, depending upon the situation.

The x-ray absorption must be such that the measured x-ray attenuation line integral in one or more given directions satisfies conditions as outlined below. With this phantom, complete point response data sets are acquired with the x-ray absorption point located at the center of each voxel in the volume of interest. In at least some implementations, the point response of a system will vary slowly with voxel position so that only a relatively small number of data sets need to be acquired and processed. Note that design of multiple point phantoms may be useful depending on the geometry and projection acquisition attributes of the system being calibrated. At an appropriate step in the analysis, the analytic extension or interpolation can be introduced.

Each point spread data set is a complete set of $0^{th}$ order point back projection visualizations $^{p\_bkp\_ijm}P$. For the calibration phantom, the point "correct" image $^{p\_cor\_ijm}P$ can be determined. For example, if the x-ray absorption point is in voxel ijm, the correct image is zero everywhere except in that voxel, where the image has a value:

$$\Sigma_{ijm} = \Sigma_{point\_material} * (\text{volume of point})/(\text{volume of voxel}). \qquad \text{EQ. 14}$$

If more than one voxel is involved, a correction image may be determined by using of one of the projections in the point spread data set and using the fact that the point is in one lamina.

Substituting as shown below, the point correction visualization for each point in the volume of interest is obtained using one of the following:

$$^{p\_\Delta ijm}I_m = {}^{p\_bkp\_ijm}I_m - {}^{p\_cor\_ijm}I_m \qquad \text{EQ. 15}$$

or $$^{p\_\Delta ijm}v^{ijm} = {}^{p\_bkp\_ijm}v^{ijm} - {}^{p\_cor\_ijm}v^{ijm}. \qquad \text{EQ. 16}$$

This approach can now be applied to determine a DVLT image of an arbitrary object using the calibrated scanning system. In particular, complete basic data set of the object is collected and a $0^{th}$ order visualization $^{bkp}I$ is created. Then, using the linearity of the DVLT algorithm, the correct scanned image for lamina "m" of the object can be obtained from:

$$^{cor}I_m = {}^{bkp}I_m - \sum_{p\_\Delta\_ijm} \left[ {}^{cor}\frac{v_{ijm}}{v_{p\_\Delta\_ijm}} \right] {}^{p\_\Delta\_ijm}I_m \qquad \text{EQ. 17}$$

The correction images $^{p\_\Delta\_ijm}I_m$ can then be normalized as follows:

$$^{p\_\Delta\_ijm}I_m = \frac{1}{v_{p\_\Delta\_ijm}} {}^{p\_\Delta\_ijm}I_m \qquad \text{EQ. 18}$$

$$^{cor}I_m = {}^{bkp}I_m - \sum_{p\_\Delta\_ijm} v_{ijm} {}^{p\_\Delta\_ijm}I_m \qquad \text{EQ. 19}$$

If the visualizations are viewed as column vectors, that is, $^{cor}I$ is considered to be a column of elements $v_{ij}$ in the image for the $m^{th}$ lamina, then EQ. 19 becomes:

$$^{cor}I_m = {}^{bkp}I_m - \sum_{p\_\Delta\_ijm} v_{ijm} {}^{p\_\Delta\_ijm}I_m \qquad \text{EQ. 20}$$

Finally, attention is directed to techniques for the evaluation of the (DVLT) algorithm for construction of digital laminar images:

$$v_j^{<n>}(\xi^{<n>} \in A_j) = v_j^{<0>} - \sum_{\xi_p^{<n>} \in A_j} K_p \xi_p^{<n>}. \qquad \text{EQ. 21}$$

Where $A = \{\xi : \pi_A(\xi)\}$,
and for $v_j \in I_m$ (which determines m), $$\xi_i^{<n>}(v^{<n-1>} \in C_{im}) = \sum_{v_p^{<n-1>} \in C_{im}} \omega_p v_p^{<n-1>}$$

where $C_{im} = B_i - I_m$ $B_i = \{v^{<0>}, \mu_B(v^{<0>})\}$.

The algorithm for DVLT and, in particular, the iteration represented by EQ. 8 above is similar to the convolution back projection techniques used in reconstruction of CT images. If the DVLT algorithm is applied to single slice CT geometry, the laminar "surfaces" are lines in the plane of the image. Moreover, if the DVLT algorithm is run to a large number of iterations, it is possible to estimate the coefficients $\kappa_p$ by equating them with those in the convolution back projection method.

As alluded to earlier, at least one alternative approach to visualization does not rely on correction visualizations or iterative processes. With attention now to FIG. 8, details are provided concerning one exemplary implementation of such an alternative approach. This process, denoted generally at 500, begins at stage 502 where two dimensional radiation transmission data is acquired for a volume of interest. Such data acquisition may proceed, for example, as disclosed herein in connection with the discussion of FIGS. 5 through 7.

The process 500 then advances to stage 504 where a set of convolution weights, or coefficients, $\gamma_p$ is obtained. As noted earlier, this set of convolution weights $\gamma_p$ can be determined computationally or empirically. At the next stage, 506, of the process 500, the convolution weights $\gamma_p$ are used in the generation of a final visualization. More particularly, the final visualization is generated as a stratigraphic back projection of the acquired two dimensional radiation transmission data. The process 500 then terminates at stage 508.

In this way, implementations of the process 500 preclude the need for iterative procedures, as the visualization is based upon the acquired set of convolution weights $\gamma_p$. More specifically, the need for error identification, and the implementation of multiple visualization correction processes, is largely precluded.

As the foregoing thus suggests, one aspect of the exemplary process 500 is that final visualization may, in some cases, be obtained relatively more quickly than would be the case where iterative processes are employed. In some instances, the relative speed with which results are obtained may not be particularly consequential, but in other cases, this relative improvement in speed proves useful.

V. Computing Environments

Embodiments of the present invention may be implemented in connection with a special purpose or general purpose computer, or other devices capable of carrying out computer-executable instructions, including various computer hardware as discussed in greater detail below, as well as controllers as disclosed herein. Embodiments within the scope of the present invention also include computer-readable media for carrying or having computer-executable instructions or electronic content structures stored thereon. Such computer-readable media can be any available media which can be accessed by a general purpose or special purpose computer.

By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or electronic content structures and which can be accessed by a general purpose or special purpose computer with multiple parallel or serial processors, or special purpose processing device such as an apparatus for radiographic image data acquisition and data and image processing.

When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and content which cause a general purpose computer, special purpose computer, or special purpose processing device, such as an apparatus for radiographic image data acquisition and data and image processing, to perform and/or cause the performance of, a certain function or group of functions.

Although not required, aspects of the invention have been described herein in the general context of computer-executable instructions, such as program modules, being executed by computers in network environments. Generally, program modules include routines, programs, objects, components, and content structures that perform particular tasks or implement particular abstract content types. Computer-executable instructions, associated content structures, and program modules represent examples of the program code means for executing steps of the methods disclosed herein. The particular sequence of such executable instructions or associated content structures represents examples of corresponding acts for implementing the functions described in such steps.

Of course, the invention may be practiced in network computing environments with many types of computer system configurations, including personal computers, hand-held devices, multi-processor systems, microprocessor-based or programmable consumer electronics, network PCs, mini-computers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment for example, program modules may be located in both local and remote memory storage devices.

The described embodiments are to be considered in all respects only as exemplary and not restrictive. The scope of the invention is, therefore, indicated by the appended claims rather than by the foregoing description. All changes which come within the meaning and range of equivalency of the claims are to be embraced within their scope.

What is claimed is:

1. A method for generating a DVLT image, the method comprising:
   acquiring a set of projection data for a volume of interest of an imaging subject, where the projection data are generated as a result of the transmission of radiation through the volume of interest by a radiation source, and the projection data comprise data concerning an attribute of the behavior of the radiation in the volume of interest;
   generating a $0^{th}$ order visualization for each lamina in the volume of interest, based upon the projection data;
   generating a first computed data set for each lamina, based upon the respective $0^{th}$ order visualizations;
   determining a first iteration correction visualization for each lamina, based upon the respective first computed data sets; and
   determining a first iteration visualization for each lamina.

2. The method as recited in claim 1, wherein the projection data comprises a plurality of data elements, each of which corresponds to a line integral of a linear x-ray attenuation coefficient along a path through the volume of interest.

3. The method as recited in claim 1, wherein the $0^{th}$ order visualization for each lamina is determined using the equation:

$$\upsilon_j^{<0>}(\xi^{<0>} \in A_j) = \sum_{\xi_p^{<0>} \in A_j} K_p \xi_p^{<0>}.$$

4. The method as recited in claim 1, wherein the first computed data set is generated using the equation:
   $D^{<1>}_m = \{\xi_1^{<1>}, \xi_2^{<1>}, \xi_3^{<1>}, \ldots\}_m$, the $i^{th}$ element of which is determined using the equation (where $\omega_p$ is a weighting factor):

$$\xi_i^{(1)}(\upsilon^{(0)} \in C_{im}) = \sum_{\upsilon^{(0)} \in C_{im}} \omega_p \upsilon_p^{(0)}.$$

5. The method as recited in claim 1, wherein the first iteration correction visualization is determined using the equation:

$$\upsilon_j^{(1)}(\xi^{(1)} \in A_j) = \upsilon_j^{(0)} - \sum_{\xi_p^{(1)} \in A_j} K_p \xi_p^{(1)}.$$

6. The method as recited in claim 1, wherein the first iteration visualization for each lamina is determined by subtracting the first iteration correction visualization for each lamina from the $0^{th}$ order visualization for the lamina.

7. The method as recited in claim 1, further comprising performing a blurring correction.

8. The method as recited in claim 1, further comprising determining at least one additional iteration visualization for each lamina.

9. The method as recited in claim 1, further comprising performing an error correction process, the error correction process comprising:
   constructing a normalizing phantom; and
   constructing a difference image based upon the normalizing phantom.

10. The method as recited in claim 1, further comprising displaying an image based upon at least the first iteration visualization for each lamina.

11. The method as recited in claim 1, further comprising displaying a volume image based upon at least the first iteration visualization for each lamina.

12. A method for generating a DVLT image, the method being suitable for use in connection with an apparatus that includes an x-ray source and a receptor, and the method comprising:
acquiring projection data for a volume of interest of an x-ray subject, where the projection data are generated as a result of the transmission of x-rays by the x-ray source through the volume of interest, and the projection data comprising a set of data elements, each of which is a measured value representing an x-ray attenuation line integral along a ray passing from an x-ray source position through the volume of interest to a receptor position;
generating a $0^{th}$ order visualization for each lamina in the volume of interest, based upon the x-ray attenuation line integrals;
generating a first computed data set for each lamina, based upon the respective $0^{th}$ order visualizations;
determining a first iteration correction visualization for each lamina, based upon the respective first computed data sets;
determining a first iteration visualization for each lamina; and
determining an additional iteration visualization for each lamina, the additional iteration visualization comprising a portion of a visual image of the volume of interest.

13. The method as recited in claim 12, wherein each x-ray attenuation line integral corresponds to an average local linear x-ray attenuation coefficient for a corresponding voxel in the volume of interest.

14. The method as recited in claim 12, wherein the $0^{th}$ order visualization for each lamina is determined using the equation:

$$v_j^{(0)}(\xi^{(0)} \in A_j) = \sum_{\xi_p^{(0)} \in A_j} K_p \xi_p^{(0)}.$$

15. The method as recited in claim 12, wherein the first computed data set is generated using the equation:
$D^{<1>}_m = \{\xi_1^{<1>}, \xi_2^{<1>}, \xi_3^{<1>}, \ldots\}_m$, the $i^{th}$ element of which is determined using the equation (where $\omega_p$ is a weighting factor):

$$\xi_i^{(1)}(v^{(0)} \in C_{im}) = \sum_{v^{(0)} \in C_{im}} \omega_p v_p^{(0)}.$$

16. The method as recited in claim 12, wherein the first iteration correction visualization is determined using the equation:

$$v_j^{(1)}(\xi^{(1)} \in A_j) = v_j^{(0)} - \sum_{\xi_p^{(1)} \in A_j} K_p \xi_p^{(1)}.$$

17. The method as recited in claim 12, wherein the first iteration visualization for each lamina is determined by subtracting the first iteration correction visualization for each lamina from the $0^{th}$ order visualization for the lamina.

18. The method as recited in claim 12, further comprising performing a blurring correction.

19. The method as recited in claim 12, further comprising performing an error correction process, the error correction process comprising:
constructing a normalizing phantom; and
constructing a difference image based upon the normalizing phantom.

20. The method as recited in claim 12, further comprising displaying an image based upon at least the first iteration visualization for each lamina.

21. The method as recited in claim 12, further comprising displaying a volume image based upon at least the first iteration visualization for each lamina.

22. A method for generating a DVLT image, the method comprising:
using a detector to acquire a set of two dimensional radiation transmission data for a volume of interest of an image subject, where the two dimensional radiation transmission data are generated as a result of the transmission of radiation through the volume of interest by a radiation source;
generating a $0^{th}$ visualization that comprises a stratiographic back projection of the two dimensional radiation transmission data;
identifying an error of the stratiographic back projection;
determining a correction visualization that comprises a back projection of a convolution of the two dimensional radiation transmission data; and
generating an error compensated visualization by subtracting the correction visualization from the $0^{th}$ visualization.

23. The method as recited in claim 22, wherein the back projection of a convolution of the two dimensional radiation transmission data corresponds to a convolution function characterized by convolution weights $\gamma_p$.

24. The method as recited in claim 22, wherein the correction visualization comprises a linear sum of component correction images.

25. A method for generating a DVLT image, the method comprising:
using a radiation detecting apparatus to acquire a set of two dimensional radiation transmission data for a volume of interest of an imaging subject;
generating a $0^{th}$ visualization that comprises a stratiographic back projection of the two dimensional radiation transmission data;
obtaining calibration data concerning the radiation detecting apparatus by way of which the two dimensional radiation transmission data is acquired; and
generating an error compensated visualization by using the calibration data to correct the $0^{th}$ visualization, where the error compensated visualization comprises a portion of a visual image of the volume of interest.

26. A computer program product for implementing a method for generating a DVLT image, the computer program product comprising:
a computer readable storage device that stores computer executable instructions for performing the method, wherein the method comprises:
acquiring a set of projection data for a volume of interest of an imaging subject, where the projection data are generated as a result of the transmission of radiation by a radiation source through the volume of interest;

generating a $0^{th}$ order visualization for each lamina in the volume of interest, based upon the projection data;

generating a first computed data set for each lamina, based upon the respective $0^{th}$ order visualizations;

determining a first iteration correction visualization for each lamina, based upon the respective first computed data sets; and determining a first iteration visualization for each lamina, the first iteration visualization comprising a portion of a visual image of the volume of interest.

27. The computer program product as recited in claim 26, wherein the projection data comprises a plurality of data elements, each of which corresponds to a line integral of a linear x-ray attenuation coefficient along a path through the volume of interest.

28. The computer program product as recited in claim 26, wherein the $0^{th}$ order visualization for each lamina is determined using the equation:

$$v_j^{(0)}(\xi^{(0)} \in A_j) = \sum_{\xi_p^{(0)} \in A_j} K_p \xi_p^{(0)}.$$

29. The computer program product as recited in claim 26, wherein the first computed data set is generated using the equation:

$D^{<1>}_m = \{\xi_1^{<1>}, \xi_2^{<1>}, \xi_3^{<1>}, \ldots\}_m$, the $i^{th}$ element of which is determined using the equation (where $\omega_p$ is a weighting factor):

$$\xi_i^{(1)}(v^{(0)} \in C_{im}) = \sum_{v^{(0)} \in C_{im}} \omega_p v_p^{(0)}.$$

30. The computer program product as recited in claim 26, wherein the first iteration correction visualization is determined using the equation:

$$v_j^{(1)}(\xi^{(1)} \in A_j) = v_j^{(0)} - \sum_{\xi_p^{(1)} \in A_j} K_p \xi_p^{(1)}.$$

31. The computer program product as recited in claim 26, wherein the first iteration visualization for each lamina is determined by subtracting the first iteration correction visualization for each lamina from the $0^{th}$ order visualization for the lamina.

32. The computer program product as recited in claim 26, wherein the method further comprises performing a blurring correction.

33. The computer program product as recited in claim 26, wherein the method further comprises determining at least one additional iteration visualization for each lamina.

34. The computer program product as recited in claim 26, wherein the method further comprises performing an error correction process, the error correction process comprising:
constructing a normalizing phantom; and
constructing a difference image based upon the normalizing phantom.

35. The computer program product as recited in claim 26, wherein the method further comprises displaying an image based upon at least the first iteration visualization for each lamina.

36. The computer program product as recited in claim 26, wherein the method farther comprises displaying a volume image based upon at least the first iteration visualization for each lamina.

37. A method for performing an imaging process, comprising:
positioning an imaging source of a first arm that is attached to a rotatable gantry so that the imaging source is arranged to direct radiation to a target volume;
positioning an imaging detector of a second arm that is attached to the rotatable gantry so that the imaging detector is arranged to receive radiation generated by the imaging source and passing through the target volume;
transmitting radiation from the imaging source through the target volume to the imaging detector; and
using the imaging detector to facilitate generation of a DVLT image by performing the following:
acquiring a set of projection data for the target volume, the projection data corresponding with the radiation received by the imaging detector;
generating a $0^{th}$ order visualization for each lamina in the target volume, based upon the projection data;
generating a first computed data set for each lamina, based upon the respective $0^{th}$ order visualizations;
determining a first iteration correction visualization for each lamina, based upon the respective first computed data sets; and
determining a first iteration visualization for each lamina.

38. The method as recited in claim 37, wherein the projection data is based on intra-fraction motion away from the target volume.

39. The method as recited in claim 37, wherein the projection data comprises a plurality of data elements, each of which corresponds to a line integral of a linear x-ray attenuation coefficient along a path of interest through the target volume.

40. The method as recited in claim 37, wherein the method is performed in connection with an imaging source that comprises a keV x-ray source.

41. The method as recited in claim 37, wherein the method is performed in connection with an imaging detector that comprises a two-dimensional detector.

42. The method as recited in claim 37, wherein one or both of the imaging source and imaging detector are moved independently of the gantry during radiation transmission.

43. The method as recited in claim 37, wherein the imaging source and imaging detector are fixed with respect to each other during radiation transmission.

44. The method as recited in claim 37, wherein the gantry rotates during radiation transmission.

45. The method as recited in claim 37, wherein one or both of the imaging source and imaging detector move in unison with the gantry during radiation transmission.

46. The method as recited in claim 37, further comprising using the first iteration visualizations as a basis for determining a parameter of a corresponding treatment beam.

47. The method as recited in claim 37, farther comprising correcting the positioning of the imaging source and imaging detector to compensate for mechanical flexure.

48. A method for performing an imaging process, comprising:
positioning an imaging source of a first arm that is attached to a rotatable gantry so that the imaging source is arranged to direct radiation to a target volume;
positioning an imaging detector of a second arm that is attached to the rotatable gantry so that the imaging detector is arranged to receive radiation generated by the imaging source and passing through the target volume;

transmitting radiation from the imaging source through the target volume to the imaging detector; and using the imaging detector to facilitate generation of a DVLT image by performing the following:

acquiring, in connection with the imaging detector, a set of two dimensional radiation transmission data for the target volume;

generating a $0^{th}$ visualization that comprises a stratiographic back projection of the two dimensional radiation transmission data;

identifying an error of the stratiographic back projection;

determining a correction visualization that comprises a back projection of a convolution of the two dimensional radiation transmission data; and generating an error compensated visualization by subtracting the correction visualization from the $0^{th}$ visualization.

49. The method as recited in claim 48, wherein the back projection of a convolution of the two dimensional radiation transmission data corresponds to a convolution function characterized by convolution weights $\gamma_p$.

50. The method as recited in claim 48, wherein the correction visualization comprises a linear sum of component correction images.

51. The method as recited in claim 48, wherein one or both of the imaging source and imaging detector are moved independently of the gantry during radiation transmission.

52. The method as recited in claim 48, wherein the imaging source and imaging detector are fixed with respect to each other during radiation transmission.

53. The method as recited in claim 48, wherein the gantry rotates during radiation transmission.

54. The method as recited in claim 48, wherein one or both of the imaging source and imaging detector move in unison with the gantry during radiation transmission.

55. A method for performing an imaging process, comprising:

positioning an imaging source of a first arm that is attached to a rotatable gantry so that the imaging source is arranged to direct radiation to a target volume;

positioning an imaging detector of a second arm that is attached to the rotatable gantry so that the imaging detector is arranged to receive radiation generated by the imaging source and passing through the target volume;

transmitting radiation from the imaging source through the target volume to the imaging detector; and using the imaging detector to facilitate generation of a DVLT image by performing the following:

acquiring, in connection with the imaging detector, a set of two dimensional radiation transmission data for the target volume;

generating a $0^{th}$ visualization that comprises a stratiographic back projection of the two dimensional radiation transmission data;

obtaining calibration data concerning one or both of the imaging detector and the imaging source; and generating an error compensated visualization by using the calibration data to correct the $0^{th}$ visualization.

* * * * *

UNITED STATES PATENT AND TRADEMARK OFFICE
CERTIFICATE OF CORRECTION

PATENT NO. : 7,737,972 B2
APPLICATION NO. : 11/403377
DATED : June 15, 2010
INVENTOR(S) : Seppi It is certified that error appears in the above-identified patent and that said Letters Patent is hereby corrected as shown below:

Patent
Change all 12 instances of "stratiographic" to --stratigraphic--

Column 1
Line 43, after "necessary to" insert --perform--

Column 2
Line 56, change "and other, aspects" to --and other aspects--

Column 4
Line 1, change "including a multiple" to --including multiple--
Line 13, change "gantry" to --gantry 102--
Line 63, change "study each" to --study for each--

Column 6
Line 66, change "the arm 174" to --the arm 186--

Column 8
Line 61, change "less radiation dose" to --lesser radiation doses--

Column 9
Line 16, change "many of problem areas" to --many of the problem areas--

Column 10
Line 41, change "one example" to --one example of--

Signed and Sealed this
Fifteenth Day of February, 2011

David J. Kappos
*Director of the United States Patent and Trademark Office*

CERTIFICATE OF CORRECTION (continued)
U.S. Pat. No. 7,737,972 B2

Column 11
Line 32, change "data be accurate" to --data should be accurate--
Line 41, change "stratigraphy" to --stratiography--
Line 48, change "x-ray ray" to --x-ray--

Column 12
Line 38, change "of algorithm" to --of the algorithm--

Column 13
Line 38, change "by convergence" to --by the convergence--

Column 15
Line 14, change "to correction" to --to the correction--

Column 16
Line 27, after "D=$\{\xi:\psi_D(\xi)\}$" insert --.--
Line 41, after "A=$\{\xi:\pi_D(\xi)\}$" insert --.--

Column 18
Line 24, change "a zero coefficients" to --zero coefficients--
Line 29, change "differences" to --that differ--

Column 19
Line 9, change "Note that design" to --Note that the design--

Column 26
Line 2, change "farther" to --further--